(12) United States Patent
Light et al.

(10) Patent No.: US 6,528,049 B2
(45) Date of Patent: Mar. 4, 2003

(54) BISEXUAL ATTRACTANTS, AGGREGANTS AND ARRESTANTS FOR ADULTS AND LARVAE OF CODLING MOTH AND OTHER SPECIES OF LEPIDOPTERA

(75) Inventors: Douglas M. Light, Davis, CA (US); Clive A. Henrick, Palo Alto, CA (US)

(73) Assignees: Trece, Inc., Salinas, CA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/840,745

(22) Filed: Apr. 23, 2001

(65) Prior Publication Data

US 2002/0061324 A1 May 23, 2002

Related U.S. Application Data

(62) Division of application No. 09/425,321, filed on Oct. 21, 1999, now Pat. No. 6,264,939.

(51) Int. Cl.[7] .......................... A01N 25/00; A01N 31/00; A01N 35/00; A01N 37/00
(52) U.S. Cl. .......................... 424/84; 43/107; 43/132.1; 424/405; 426/1; 514/529; 514/546; 514/549; 514/552; 514/693; 514/703; 514/715; 514/724; 514/739
(58) Field of Search .............................. 43/108, 132.1; 43/107; 426/1; 424/84, 405; 514/546, 549, 552, 693, 703, 715, 724, 739, 529

(56) References Cited

U.S. PATENT DOCUMENTS

| 3,891,759 A | * | 6/1975 | Aries .......................... 514/136 |
| 3,953,377 A | * | 4/1976 | Naf ............................. 512/126 |
| 5,447,718 A | * | 9/1995 | Aldrich et al. ................. 424/84 |

OTHER PUBLICATIONS

Yokoyama et al., 'A Plum Volatile, 1–Nonanol: An Oviposition Deterrent for Codling Moth' (Can. Entomol. (123, No. 3, 711–12, 1991), STN/CAS online, file CROPU, Abstract.*

Rhainds et al., 'Chiral esters: Sex pheromone of the bagworm, *Oiketicus kirbyi* (Lepidoptera: Psychidae' (Journal of Chemical Ecology, (1994) vol. 20, No. 12, pp. 3083–3096), STN/CAS online, file BIOSIS, Abstract.*

STN/CAS online, file CAPLUS, Acc. No. 1987:596730, Doc. No. 107:196730 (Pretorius et al., Dtsch. Lebensm.–Rundsch.(1987), vol. 83, No. 6, pp. 180–182), Abstract.*

* cited by examiner

*Primary Examiner*—Jose G. Dees
*Assistant Examiner*—Frank Choi
(74) *Attorney, Agent, or Firm*—Hana Verny

(57) ABSTRACT

Novel bisexual attractants for lepidopterous insect pests isolated from pears or apples. A method for monitoring and control of codling moth and other species of Lepidoptera comprising a lure and kill, mating disruption or mass trapping strategy. A method of using a formulation containing the bisexual attractants with or without an insecticide and/or pheromone for control of the insect pests.

14 Claims, 13 Drawing Sheets

BISEXUAL ATTRACTANTS, AGGREGANTS AND ARRESTANTS FOR ADULTS AND LARVAE OF CODLING MOTH AND OTHER SPECIES OF LEPIDOPTERA

This is a divisional of U.S. application Ser. No. 09/425,321, filed on Oct. 21, 1999, now issued as U.S. Pat. No. 6,264,939.

BACKGROUND OF THE INVENTION

1. Field of the Invention

This invention concerns novel bisexual attractants for codling moth and other species of Lepidoptera. In particular, the invention concerns attractants isolated from pear or apple volatiles which have superior and selective attractancy for adult codling moths and other lepidopterous species. These attractants also attract, aggregate and/or arrest larvae of these species. The invention further concerns a method for monitoring, control, mass trapping and mating disruption of codling moth and other lepidopterous species. The method includes luring the pest to a formulation containing the attractant, aggregant or arrestant of the invention, alone, or in combination with a sex pheromone and/or another kairomone and/or insecticide.

2. Background and Related Disclosures

Insect pests, particularly insects of the order Lepidoptera, such as codling moth, are responsible for substantial losses of fruit and nut crops. Currently, the most often utilized systems for monitoring and controlling these insect pests are compositions comprised of an attractant, almost always a sex pheromone attractant, optionally in combination with an insect killing substance, such as an insecticide. The majority of the baits or traps utilize sex pheromones that attract only males. While these traps and baits provide a certain degree of monitoring information and control, they are not effective in attracting the females, which are responsible for reproduction, nor larvae, which are responsible for damaging fruits and nuts.

Semiochemicals are behavior modifying chemicals acting as chemical signals that elicit certain behaviors from other individuals of either the same species (i.e., pheromones) or from other species (i.e., kairomones and allomones). The best known semiochemicals are pheromones.

Over 1600 insect pheromones have now been identified. Typically, the sex pheromones are produced and released by females at the time of mating to attract conspecific male insects. Since females are responsible for laying eggs and since each female may lay large numbers of eggs during one season, it is very important to monitor and control females in addition to males. The sex pheromones used in lures or baits, however, in general, only attract the male insect. Thus, the real purpose of luring or killing insect pests is unfulfilled because even one fertile female may lay enough eggs to substantially infest a large area. Also, lures and baits for larvae are needed which would intercept and kill the larvae before they damage fruit and nut crops.

The use of sex pheromones for attracting and killing an insect pest is thus of limited utility. It would be very advantageous to provide substances which would attract males and attract and/or modify the behavior of females and/or their larval offspring.

Kairomones, the second type of semiochemicals, are typically odoriferous volatile compounds from plants, which are recognized by the insect pests and aid them in locating suitable host plants. Their value as insect pest attractants has been previously recognized and many attempts were made to utilize kairomones as insect pest attractants. The primary advantage of kairomones is that in most cases they attract both males and females. However, typically they are not very well detected by individual insect species and, therefore, lack general utility as useful attractants.

Chemotropic utility of various fermenting baits was already recognized in 1943, when molasses and yeast containing baits with or without the addition of shelf chemicals were tested for their chemotropic utility. This work is described in *J. Econ. Entomology*, 36: 430 (1943).

The unrelated and chemically distinct sesquiterpene, (E,E)-α-(-farnesene has been recognized as a larval attractant since 1972, as described in *Nature*, 239:170 (1972).

Sensitivity of antennae of male and female insect of the order of Coleoptera was studied with regard to conspecific aggregation pheromones, allomones and host-produced odorants. The lowest antennal sensitivity was observed for host produced odorants (*J. Chem. Ecol.*, 9:585 (1983)).

Attractivity of volatile components of starthistle flower for flies and weevils was described in *J. Agric. Food Chem.*, 34: 786 (1986). Tomato leaf volatile aroma components are described in *J. Agric. Food Chem.*, 35: 1039 (1987).

Electroantennogram responses of the oriental fruit fly to a spectrum of alcohol and aldehyde plant volatiles are described in *Entomologia Experimentalis et Aplicata*, 45: 55 (1987) and in *J. Chem. Ecol.*, 14: 159 (1988), and to volatile constituents of nectarines in *Entomol. Exp. Appl.* 63: 13 (1992). *J. Chem. Ecol.*, 22: 1735 (1996) describes electroantennogram responses of Lepidoptera to volatile compounds from moth-pollinated flowers. Headspace examination of volatile emission of organic compounds from ripening papaya is described in *J. Agric. Food Chem.*, 38: 105 (1990).

*Chemoecology*, 4: 175 (1993) describes enhancement of sex pheromone attraction with green leaf volatiles for tobacco budworm. The synergistic effect of host-plant green-leaf on the synthetic sex pheromones of the corn earworm and codling moth is described in *Chemoecology*, 4: 145 (1993).

Plant volatiles were shown to evoke and modulate tephritid behavior (*Fruit Fly Pests*, Part II, 123–134 (1996), Eds. McPheron, B. and Steck G., St. Lucie Press, Debray Beach, Fla.).

U.S. Pat. No. 5,665,344 describes volatiles of Japanese honeysuckle flowers as attractants for adult lepidopterous insects.

However, as described in all the above references, the host-plant volatiles are typically used in combinations of several volatiles and these mixtures show weak attractancy over the background plant volatile odors that are present in the environment.

It would, therefore, be advantageous to provide semiochemicals which would attract adult insects of both sexes and the larvae, but primarily, which would attract the female insect responsible for reproduction and attract, aggregate or arrest the larvae responsible for crop damage.

It is, therefore, a primary objective of the current invention to provide semiochemical kairomonal attractants which would strongly attract both the female and male adult insect pests as well as the larvae to monitoring traps, lure-kill traps or baits and in this way attract, aggregate, arrest and/or kill the adult males and particularly the adult reproductive females and the larvae and which would also provide monitoring tools and control and protection of crops from the insect pest.

All patents, patent applications and publications cited herein are hereby incorporated by reference.

SUMMARY

One aspect of the current invention is a novel class of bisexual attractants for the codling moth (*Cydia pomonella*) and other lepidopterous species.

Another aspect of the invention is a bisexual attractant selective for female codling moth which is present in the odors and extracts of pome fruits.

Another aspect of the current invention is an attractant, aggregant or arrestant for larvae of lepidopterous species, particularly codling moth, which is present in the odors and extracts of pome fruits.

Still another aspect of the current invention are compounds, represented by pure ethyl (2E,4Z)-2,4-decadienoate or an isomer or a derivative thereof, which are bisexual adult attractants and larvae worm attractants, aggregants or arrestants for codling moth and other species of Lepidoptera.

Still yet another aspect of the current invention is a method for monitoring, control, mass trapping, and disruption of codling moth mating and invasion of fruit orchards and for protection of fruit crops, particularly pear, apple and walnut crops from the adult insects and larvae.

Still yet another aspect of the current invention is a method for capture of and elimination of codling moth by attracting both the female and male insects as well as the larvae by providing a formulation comprising a kairomonal attractant derived from the pear or apple, alone, or in a combination with a sex pheromone, other kairomone and/or insecticide.

Still yet another aspect of the current invention is a formulation placed in a lure-kill trap or a bait comprising a kairomone attractant derived from the pear or apple, alone, or in a combination with a sex pheromone, other kairomone and/or insecticide, or in admixture with other volatile compounds for attracting, aggregating or arresting adult insects and larvae of lepidopterous species wherein said formulation is in a sprayable, solid or liquid form or in a time release form and wherein said formulation is placed in a trap, trap-like station, trap-like enclosure or trap-like platform.

Still another aspect of the current invention is a lure-kill trap or bait comprising a kairomone attractant derived from the pear or apple, alone, or in a combination with a sex pheromone, other kairomone and/or insecticide.

Still another aspect of the current invention are purified compounds isolated from a pear extract, their isomers or derivatives purified up to at least 90% purity which are attractants, aggregants or arrestants for adult insects and larvae of lepidopterous species, said attractant, aggregant or arrestant comprising one or more pear extract components.

DEFINITIONS

Figure 1:
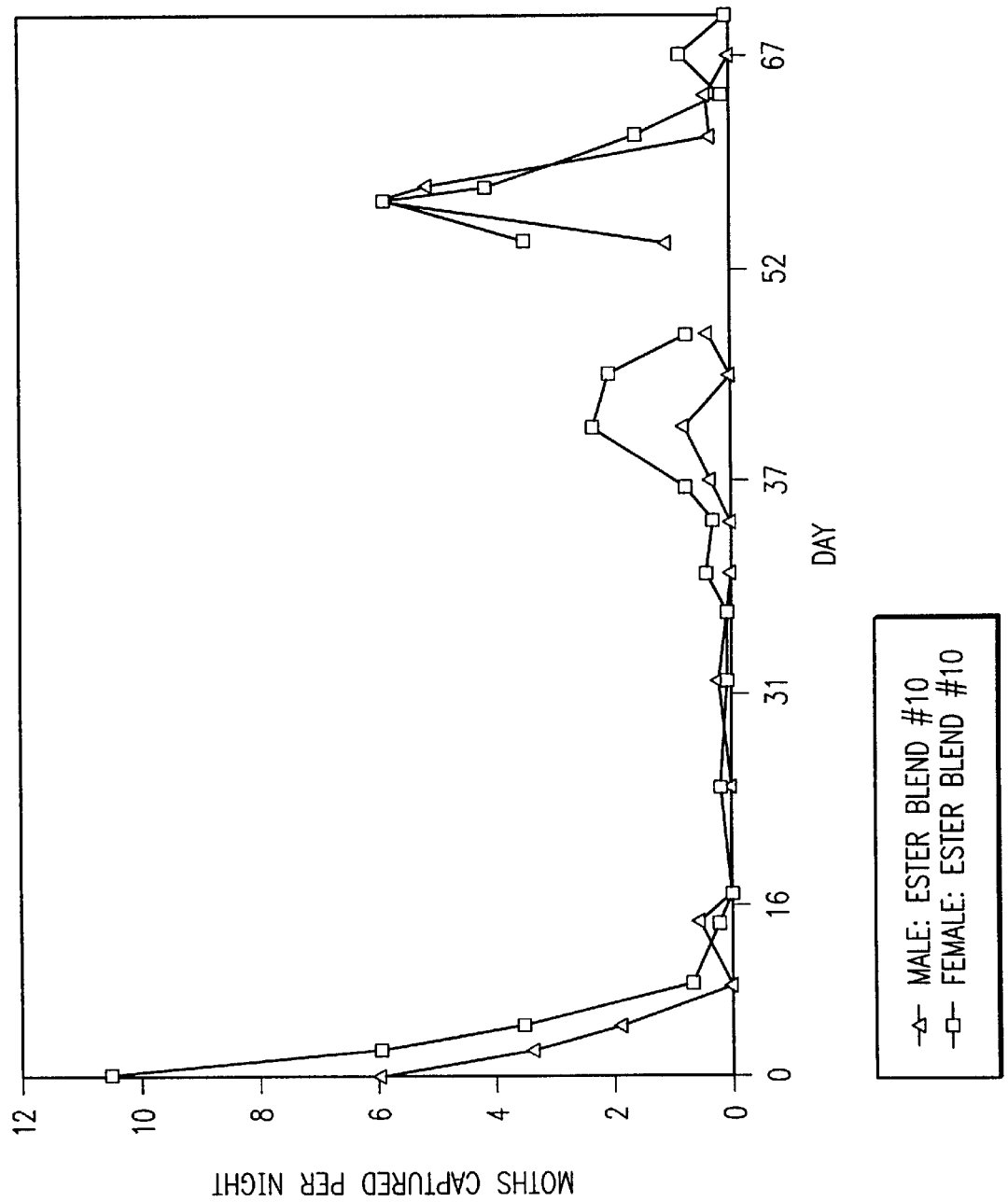
FIG. 1 is a graph depicting attraction of female and male codling moths to a synthetic pear extract blend (ester blend #10) supplied in the baited sticky trap. Male codling moth (-Δ-), female codling moth (-□-).

As used herein:

"Extract blend" means a mixture of more than two components found in the volatiles isolated from pome fruits, such as pears, apples, etc., or a mixture of at least one of such components in admixture with other components such as pheromones, alcohols, esters or other additives. The blend may also contain insecticide.

"Pheromone" or "sex pheromone" means an intraspecific signal molecule, and typically in Lepidoptera produced and released by female insects at the time of, or prior to mating, that attracts males.

"Insect pest" means any lepidopterous species, particularly codling moth, which attacks pome fruit and nut trees.

"HPV" means host-plant volatile.

"Kairomone" means an interspecific semiochemical signal molecule that typically is an odoriferous volatile compound, released by plants, which is detected and recognized by the insect and aids them in locating a suitable host plant.

"Attractant" means a compound falling within a formula shown in Section 1A, that causes the adult males and/or females and/or larvae of the lepidopterous species to make oriented movement towards the compound.

"Aggregant" means a compound falling within a formula shown in Section 1A that causes males and/or females and/or larvae of the lepidopterous species to aggregate or accumulate at a site containing the compound and remain there for a period.

"Arrestant" means a compound falling within a formula shown in Section 1A, that causes the males and/or females and/or larvae of the lepidopterous species to aggregate upon contact with said compound. The arrestant typically shows the linear progression of the organism by reducing actual speed of locomotion or by increasing the turning rate.

"Ovipositional stimulant" or "feeding stimulant" means a compound falling within a formula shown in Section 1A, that elicits feeding or oviposition in the males and/or females and/or larvae of the lepidopterous species.

DETAILED DESCRIPTION OF THE INVENTION

This invention concerns the discovery that volatile semiochemicals derived from pome fruits, such as pears or apples, are superior bisexual attractants, and that in addition to attracting males, they also attract, specifically and differentially, the female codling moths or other species of Lepidoptera and additionally act as attractants, aggregants and arrestants for larval stages of the codling moth or other Lepidoptera species. These novel attractants are superior to other known kairomonal attractants. These novel kairomonal attractants provide and are useful in methods for monitoring, controlling, mass trapping and mating disruption of adult insect pests, for arresting or aggregating larval growth and development, and for controlling the infestation of fruit orchards, such as apple, pear and walnut orchards by the adult insects or larvae.

These findings were unexpected and surprising because while the codling moth is known to be attracted to and attacks the nonripened fruit, the novel attractants of the invention are derived from the ripened mature fruit. As described below, the new attractants of the invention, which are found in ripened fruit, are different from host plant volatile compounds found in nonripened fruit, a target of the insect and/or larval invasion.

This invention was developed in order to achieve effective monitoring, control and management of moth pests and other fruit tree-infesting insects and larvae. The aim of the invention was to control and manipulate moth behavior, such as feeding, attraction, mating, oviposition and also larval development.

Current means of monitoring the occurrence, population levels, and flight pattern of moth pests is solely by pheromone trap-catching of adult male moths. The first aim of the invention, therefore, was to identify female attractants because it is the egg-laying of female moths that determines the damage potential of the next larval generation.

Current pheromone-based mating disruption control of codling moth was found to be in need of improvement in efficacy. Female moths perform all their sexual-reproductive activities such as calling, courtship, mating and oviposition, while perched on their host-plants. Host plant volatiles (HPVs) continuously and simultaneously evaporate from the plant leaf and fruit substrates while the female moth calls and emits her pheromone. Thus, pheromones and HPVs always share the same environmental context and might be adaptively associated in chemoreception and behavior by the male moths.

The second aim of the invention, therefore, was to discover and develop the use of these volatile attractants to enhance the attractancy of already existing sex pheromones, and their specificity and effectiveness for monitoring and mating disruption of insect pest populations.

As described in greater detail below, a group of compounds which attracts adult females and males as well as the larvae have now been identified. Such identification of female and larvae attractants allow for the development of novel monitoring tools and direct control tactics aiding in the monitoring of appropriate timing of control measures, or directly disrupting population levels, flight pattern, mating and oviposition of female codling moth and other lepidopterous species in walnut, apple, pear or other fruit and nut orchards. The newly discovered attractants for adult insect were additionally found to attract the larvae, and cause their aggregation in the vicinity of these compounds.

Since the substantial damage to the fruit and nut trees is done by larval codling moth and other lepidopterous species, the third aim of the invention was to investigate if the compounds of the invention found in ripened fruit of some fruits trees were also attracting or otherwise affecting growth and development of the larvae.

I. Semiochemical Attractants

Semiochemical attractants of the invention are volatile kairomones isolated from ripe pear, apple, quince or other pome fruit trees, which are unique, host-derived attractants that specifically attract both larvae and adult insect pests of the order Lepidoptera, particularly the codling moth, and still more specifically, which attract adult codling moths in various female to male ratios, depending on the time in the season. While the new host volatile attractants are isolated from the ripened pome fruits, they attract both adult insects and larvae when placed in orchards containing unripened fruits, which do not exude the host plant volatiles of the invention.

These newly discovered attractants have a surprisingly very high competitive potency, ranging from approximately 50% to equal or greater the attractancy of the synthetic commercial pheromone (E,E)-8,10-dodecadienol, from early-season to mid- and late-season. The attraction of females to the new attractant is not affected or disrupted by the simultaneous presence of conspecific synthetic male sex pheromone. This discovery was surprising and of a significant value because until now there were no known effective female and larval attractants for codling moth or most other species of Lepidoptera.

A. Host-plant Volatile Kairomonal Attractants

The novel attractants for Lepidoptera are host plant-volatile derived kairomonal attractants. These attractants were isolated and identified from ripe non-nut, pome fruit host-plants, primarily from ripe pears, apples, quince and other fruit volatile extracts. The active attractants were collected and chemically identified by GC-MS from headspace odor emission of the pear and apple host-trees. Typically, the active attractants comprise one or more compounds. The attractant compounds were further identified as esters, such as ethyl (2E,4Z)-2,4-decadienoate, its geometrical and positional isomers and derivatives, and related compounds such as allenes, other decadienoates, decanoates, decenoates, dodecadienoates and decatrienoates. Where appropriate, optical isomers of these esters are also included. Representative exemplary compounds of the new attractants are methyl or ethyl decanoate, methyl or ethyl (E)-2-decenoate, methyl or ethyl (Z)-4-decenoate, methyl (2E,4Z)- or (2E,4E)-2,4-decadienoate, ethyl (2E,4Z)- or (2Z,4Z)- or (2E,4E)- or (2Z,4E)-2,4-decadienoate, propyl (2E,4Z)- or (2E,4E) -2,4-decadienoate, ethyl 2,4-dodecadienoates, ethyl 2,4,6-decatrienoates and other derivatives as described to be present in the fresh apples, apple juices and cooked apples, in the Bartlett and other types of pears and in quince, all listed in *Volatile Compounds in Food*, TNO Nutrition and Food Research Institute, The Netherlands, Seventh Edition (1996), Index of Compounds, 1.1–1.18 for apples, 13.1–13.5 for pears and 125.1–125.6 for quince, hereby incorporated by reference in its entirety.

Any and all compounds listed in the above identified Index of Compounds are intended to be within the scope of the method of this invention as long as they possess attractant properties for adult and/or larval lepidopterous species.

Generally, the attractant will have a general formula

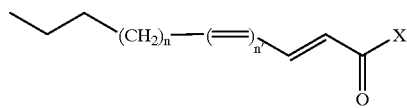

wherein n is an integer 0–8;
wherein n' is an integer 0, 1 or 2;
wherein X is $OR_1$, $NR_1R_2$, $SR_1$ or $R_1$; wherein $R_1$ is H or alkyl C1 to C6 and $R_2$ is H or alkyl C1-C6.
Preferred compounds have formulae

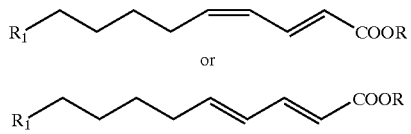

wherein R and $R_1$ are —$CH_3$, —$CH_2CH_3$ or $CH_2CH_2CH_3$.

Representative compounds were obtained from the headspace volatiles of the fruit trees by passing the air over and collecting the odorous vapors or by extracting the fruit, ripened or nonripened, with an organic solvent or by steam distillation. The compounds were prepared as mixtures of two or more compounds or as individual purified compounds. These compounds were tested and additionally compared to commercially available synthetic products.

The representative compounds acting as attractants for adult female and male insect and larvae of codling moth and/or other lepidopterous species are:

Ethyl (2E,4Z)-2,4-decadienoate as a mixture;
Ethyl (2E,4Z)-2,4-decadienoate purified;
Ethyl (2E,4E)-2,4-decadienoate purified;
Ethyl (2Z,4E)2,4-decadienoate purified;
Ethyl (2Z,4Z)-2,4-decadienoate purified
Methyl (2E,4Z)-2,4-decadienoate purified;
Methyl (2E,4E)-2,4-decadienoate purified;
Propyl (2E,4Z)-2,4-decadienoate purified;
Propyl (2E,4E)-2,4-decadienoate purified;
Butyl (2E,4Z)-2,4-decadienoate purified;
Butyl (2E,4E)-2,4-decadienoate purified;
Pentyl (2E,4Z)-2,4-decadienoate purified;
Pentyl (2E,4E)-2,4-decadienoate purified;
Hexyl (2E,4Z)-2,4-decadienoate purified;
Hexyl (2E,4E)-2,4-decadienoate purified;
Isopropyl (2E,4Z)-2,4-decadienoate purified;
Isopropyl (2E,4E)-2,4-decadienoate purified;
Ethyl (2E,4Z)-2,4-dodecadienoate as a mixture;
Ethyl (2E,4E)-2,4-dodecadienoate purified;
Ethyl (2E,4Z)-2,4-dodecadienoate purified;
Methyl (2E,4Z)-2,4-dodecadienoate purified;
Methyl (2E,4E)-2,4-dodecadienoate purified;
Propyl (2E,4Z)-2,4-dodecadienoate purified;
Propyl (2E,4E)-2,4-dodecadienoate purified;
Butyl (2E,4Z)-2,4-dodecadienoate purified;
Butyl (2E,4E)-2,4-dodecadienoate purified;
Pentyl (2E,4Z)-2,4-dodecadienoate purified;
Pentyl (2E,4E)-2,4-dodecadienoate purified;
Hexyl (2E,4Z)-2,-dodecadienoate purified;
Hexyl (2E,4E)-2,4-decadienoate purified;
Isopropyl (2E,4Z)-2,4-dodecadienoate purified; and
Isopropyl (2E,4E)-2,4-dodecadienoate purified.

The isolated compounds were purified to 90–100%, preferably to over 98% purity, by a method described in Example 3.

Volatile attractants of the invention were investigated for their respective percentile presence in the odor of either immature, unripe pears or store-bought ripe pears (1 kg) both trapped for about 11 hours under 1 L/minute air stream and their odors or vapors were collected and analyzed. Results are shown in Table 1A (ripe pears host-plant volatiles and in Table 1B (immature, unripe pears host-plant volatiles).

Table 1A shows their respective percentile representation of host-plant volatiles obtained from store bought, fully ripe cut or whole pears.

TABLE 1A

Ripe Pears Host Plat Volatiles

| # | Cut % | Whole % | Compound |
|---|-------|---------|----------|
| 1 | 0.69 | 0.58 | 1-butanol |
| 2 | 0.22 | 0.04 | acetoin (3-hydroxybutan-2-one) |
| 3 | 0.02 | + | ethyl propanoate |
| 4 | 1.41 | 0.76 | propyl acetate |
| 5 | 0.2 | 0.03 | methyl butyrate |
| 6 | 0.18 | 0.06 | 2-methyl butan-1-ol |
| 7 | 0.32 | 0.06 | isobutyl acetate |
| 8 | 0.57 | + | n-hexanal |
| 9 | 0.09 | 0.13 | ethyl butyrate |
| 10 | 31.41 | 27.73 | butyl acetate |
| 11 | 0.14 | 0.29 | hexanol |
| 12 | 0.09 | 0.08 | 2-methylbutyl acetate |
| 13 | 1.36 | 0.86 | pentyl acetate |
| 14 | 0.13 | 0.03 | methyl caproate |
| 15 | 0.03 | + | 6-methyl-5-hepten-2-one |
| 16 | 0.03 | 0.04 | butyl butyrate |
| 17 | 0.38 | 0.15 | ethyl caproate (hexanoate) |
| 18 | 0.08 | 0.05 | (Z)-3-hexenyl acetate |
| 19 | 31.64 | 27.12 | hexyl acetate |
| 20 | 0.02 | + | ethyl heptanoate |
| 21 | 0.14 | 0.26 | |
| 22 | 0.22 | 0.12 | heptyl acetate |
| 23 | 0.05 | 0.02 | methyl octanoate (caprylate) |

TABLE 1A-continued

Ripe Pears Host Plat Volatiles

| # | Cut % | Whole % | Compound |
|---|-------|---------|----------|
| 24 | 0.05 | 0.02 | methyl 2-octenoate |
| 25 | 0.03 | + | |
| 26 | 0.02 | + | |
| 27 | 0.17 | 0.19 | estragole (allyl anisole) |
| 28 | + | 0.07 | butyl hexanoate |
| 29 | 0.21 | 0.25 | hexyl butyrate |
| 30 | 0.22 | 0.1 | ethyl caprylate octanoate |
| 31 | 0.17 | 0.25 | |
| 32 | 0.16 | 0.15 | octyl acetate |
| 33 | 0.02 | + | |
| 34 | 0.12 | 0.08 | ethyl (E)-2-octenoate |
| 35 | 0.01 | 0.03 | |
| 36 | 0.03 | + | |
| 37 | 0.03 | 0.06 | t-anethole |
| 38 | 0.12 | 0.23 | cyclodecanone (int. Std.) |
| 39 | 0.69 | 0.19 | methyl (Z)-4-decenoate |
| 40 | 0.03 | + | methyl decenoate |
| 41 | 0.02 | + | |
| 42 | 0.05 | + | methyl 2-decenoate |
| 43 | 0.04 | + | |
| 44 | 1.61 | 0.28 | ethyl 4-decenoate |
| 45 | 0.55 | 0.53 | |
| 46 | 7.5 | 5.15 | methyl (2E,4Z)-decadienoate |
| 47 | 0.05 | 0.03 | α-copaene |
| 48 | 0.13 | 0.03 | ethyl caprate (decanoate) |
| 49 | 0.02 | 0.19 | tetradecane |
| 50 | 0.02 | + | |
| 51 | 0.12 | 0.06 | ethyl t-2-decenoate |
| 52 | 0.04 | 0.04 | ethyl (E,E)-2,4-decadienoate |
| 53 | 0.81 | 1.2 | |
| 54 | 11.4 | 10.04 | ethyl (2E,4Z)-2,4-decadienoate |
| 55 | + | 0.03 | |
| 56 | 0.49 | 0.64 | (Z,E)-α-farnesene |
| 57 | 5.2 | 20.53 | (E,E)-α-farnesene |
| 58 | 0.05 | 0.19 | pantadecane |
| 59 | 0.11 | 0.13 | d-cadinene |
| 60 | 0.02 | + | |
| 61 | 0.02 | + | |
| 62 | 0.03 | 0.07 | |
| 63 | + | 0.03 | |
| 64 | 0.03 | + | |
| 65 | + | 0.03 | |
| 66 | + | 0.03 | |
| 67 | + | 0.03 | |
| 68 | + | 0.04 | |
| 69 | 0.12 | 0.39 | hexadecane |
| 70 | 0.02 | | |
| 71 | 0.03 | 0.09 | |
| 72 | 0.02 | | |
| 73 | 0.01 | 0.03 | heptadecane |
| 74 | 0.03 | 0.12 | |
| 75 | 0.04 | 0.06 | |
| 76 | 0.02 | | dibutylphthalate |
| 77 | 0.02 | | |
| | 100.09 | | |

As seen in Table 1A, seventy seven individual compounds were found to be present in the pear extract or headspace odor from cut or whole store bought ripe pears. Of these, about 50 individual compounds were identified. Of these compounds, only seven compounds were found to be present in both ripe (Table 1A) and immature Bartlett odor pear (Table 1B).

For ripe pear odor (Table 1A) twenty-seven compounds, present only in trace amounts, were not identified. The relative percentile of the identified compounds ranged from minute amounts of about 0.02%, for example compounds 3, 20 and 33, to rather large amounts of about 30%, for example compounds 10, 19 and 57. The compound 54, which is the most active and therefore preferred codling moth attractant, was found to be represented by around 11% in the volatile from the cut pears and about 10% in the volatile from the whole pear. This compound (54) was not detected to be present at all in immature apples or pears (Table 1B).

Using different isolating methods, these and other compounds may be isolated from the ripe pome fruit and may possess attractant properties for Lepidoptera. All of these compounds are contemplated to be within the scope of the invention.

Table 1B shows the percentile representation of host plant volatiles obtained in three experiments from mid-summer picked, immature, nonripe whole Bartlett pears, Golden Delicious apples, and Granny Smith apples.

TABLE 1B

Immature Unripe Host-Plant Volatiles

| | | Immature Apples: | |
|---|---|---|---|
| Compounds | Immature (Green): Bartlett Pear | Golden Delicious (%) | Granny Smith (%) |
|---|---|---|---|
| 1 Ethyl Acetate | 0.64 | | |
| 2 Propyl Acetate | 0.21 | | |
| 3 Butyl Acetate | 1.06 | | |
| 4 Hexanal | 0.21 | 1.33 | 1.79 |
| 5 Isobutanol | 0.85 | | |
| 6 (Z)-3-Hexanal | 0.21 | 3.29 | 4.55 |
| 7 3-Methylbutanol | 0.85 | | |
| 8 (E)-2-Hexanal | 0.64 | 4.5 | 8.49 |
| 9 (Z)-β-Ocimene | | 0.16 | 0.28 |
| 10 (E)-β-Ocimene | 1.49 | 3.29 | 24.6 |
| 11 Hexyl Acetate | | 0.62 | 0.79 |
| 12 (E)-4,8-Dimethyl-1,3,7-nonatriene | | 28.7 | 20 |
| 13 (Z)-Hexenyl Acetate | | 11.42 | 5.16 |
| 14 (Z)-Pentenol | 0.20 | 0.57 | 0.55 |
| 15 (E)-2-Hexenyl Acetate | | 0.24 | 0.61 |
| 16 Hexanol | 0.21 | 0.88 | 1.24 |
| 17 (Z)-3-Hexenol | 0.64 | 5.19 | 4.25 |
| 18 (E)-2-Hexenol | | 0.52 | 1.73 |
| 19 Acetic Acid | | 2.6 | 2.03 |
| 20 α-Copaene | 0.43 | | |
| 21 Benzaldehyde | 0.21 | | |
| 22 2,3-Butandiol | 34 | | |
| 23 Meso 2,3-Butandiol | 40.4 | | |
| 24 (Z)-3-Hexenyl Butyrate | | 1.51 | 0.29 |
| 25 Linalool | | 6.58 | 3.94 |
| 26 Caryophyllene | 1.28 | 0.35 | 1.09 |
| 27 2-Methylbutyric Acid | 1.06 | | |
| 28 Humulene | 0.43 | | |
| 29 Germacrene-D | 0.06 | 0.67 | 1 |
| 30 (Z,E)-α-Farnasene | | 0.42 | 0.21 |
| 31 (E,E)-α-Farnasene | 10.6 | 22.5 | 12.4 |
| 32 δ-Cadinene | 1.28 | 0.35 | 0.64 |
| 33 Methyl Salicylate | | 1.73 | 2.34 |
| 34 2-Phenylethanol | 0.21 | 0.42 | 0.68 |
| 35 Penylacetonitrile | 0.85 | 0.73 | 0.85 |
| 36 (Z)-3-Hexenyl Benzoate | | 1.44 | 0.49 |
| 37 2-ethylpropyl Tetradecanoate | 2.13 | | |

As seen in Table 1B, 37 compounds were identified in immature unripe host-plant volatiles in Bartlett pear or in Golden Delicious or Granny Smith apples. As pointed out above, only seven compounds were found to be present in both ripe and immature fruits. None of these compounds belongs to the group of ester compounds, namely, alkyl decanoates, decenoates, dodecanoates, etc., identified as lepidopterous attractants, aggregants or arrestants.

The codling moth lays eggs on, attacks and infests only immature apple and pear fruits that reside on the tree during the summer season, from May through September in the Northern Hemisphere. These susceptible fruits remain in an unripe state while they grow in size and maturity on the tree. Pome fruits are classified as climacteric fruits meaning they will not ripen, soften nor enrich in odor/flavor until they have been picked from the tree. Once ripe, pome fruits have advanced to a stage that is unsuitable as a host for codling moth or other moth infestation. Table 1B shows the typical compositional odor of both immature pears and apples. For immature pears, Table 1B identifies twenty-five compounds ranging from simple aliphatic aldehydes, alcohols and acetates to numerous terpenes both monoterpenes and sesquiterpenes; but no ester compounds were identified that are so indicative of the odor of ripe pears (Table 1A).

B. Mixtures of Attractants with Additives

In the method for attracting larvae and adult female and male codling moths or other lepidopterous species fruit-tree insect pests, the attractants of the invention are utilized either as individual, purified compounds, or as mixtures of several synthetic or natural purified compounds, or as a partially purified or nonpurified natural or synthetic mixtures.

The attractants of the invention are used and applied alone individually or in a mixture of two or more attractants or in combination with additives, such as the codling moth sex pheromone, to additionally attract the male codling moth, or a pheromone specific to the lepidopterous species to be captured. The attractant may further be used in combination with one or more insecticides for use in attract-kill baits or traps or in formulations according to the method of the invention and/or in combination with other kairomones, allomones, synomones and other additives or formulating agents.

C. Additives

Additives suitable for combination with the attractants of the invention are primarily the male sex pheromones of codling moth or other lepidopterous species and insecticides, but also include such formulating agents as emulsifiers, UV absorbers and UV blocking agents, antioxidants, viscosity regulating agents, inert solvents, buffers, diluents and other auxiliary compounds typically used in these types of formulations.

1. Sex Pheromones

The sex pheromone is the semiochemical molecule produced and released by the female insect pest signaling her receptivity to mating. The sex pheromone is the cue that attracts the male insect. Because the attractant of the invention attracts both sexes, the addition of the sex pheromone to the attractant of the invention is optional. The addition of pheromone to the attractant enhances the male attraction to the attractant-containing lure and thus further assures that it is not only the egg-laying females that are attracted to the trap or bait but that also the majority of the male insects are attracted. This approach further protects the fruit and nut tree and orchards from damaging pest infestations.

The following pheromones, for example, may be used within the scope of the present invention:

(Z)-5-decenyl acetate, dodecanyl acetate, (Z)-7-dodecenyl acetate, (E)-7-dodecenyl acetate, (Z)-8-dodecenyl acetate, (E)-8-dodecenyl acetate, (Z)-9-dodecenyl acetate, (E)-9-dodecenyl acetate, (E)-10-dodecenyl acetate, 11-dodecenyl acetate, (Z)-9,11-dodecadienyl acetate, (E)-9,11-dodecadienyl acetate, (Z)-11-tridecenyl acetate, (E)-11-tridecenyl acetate, tetradecanyl acetate, (E)-7-tetradecenyl acetate, (Z)-8-tetradecenyl acetate, (E)-8-tetradecenyl acetate, (Z)-9-tetradecenyl acetate, (E)-9-tetradecenyl acetate, (Z)-10-tetradecenyl acetate, (E)-10-tetradecenyl acetate, (Z)-11-tetradecenyl acetate, (E)-11-tetradecenyl acetate, (Z)-12-pentadecenyl acetate, (E)-12-pentadecenyl acetate, hexadecanyl acetate, (Z)-7-hexadecenyl acetate, (Z)-11-hexadecenyl acetate, (E)-11-hexadecenyl acetate, octadecanyl acetate, (E,Z)-7,9-dodecadienyl acetate, (Z,E)-7,9-dodecadienyl acetate, (E,E)-7,9-dodecadienyl acetate, (Z,Z)-7,9-dodecadienyl acetate, (E,E)-8,10-dodecadienyl acetate, (E,Z)-9,12-dodecadienyl acetate, (E,Z)-4,7-tridecadienyl acetate, (E,E)-9,11-tetradecadienyl acetate, (Z, Z)-9,12-tetradecadienyl acetate, (Z,Z)-7,11-hexadecadienyl acetate, (E,Z)-7,11-hexadecadienyl acetate, (Z,E)-7,11-hexadecadienyl acetate, (E,E)-7,11-hexadecadienyl acetate, (Z,E)-3,13-octadecadienyl acetate, (E,Z)-3,13-octadecadienyl acetate, (E,E)-3,13-octadecadienyl acetate, decanol, (Z)-6-nonenol, (E)-6-nonenol, dodecanol, (Z)-5-decenol, 11-dodecenol, (Z)-7-dodecenol, (E)-7-dodecenol, (Z)-8-dodecenol, (E)-8-dodecenol, (E)-9-dodecenol, (Z)-9-dodecenol, (E)-9,11-dodecadienol, (Z)-9,11-dodecadienol, (Z,E)-5,7-dodecadienol, (E,E)-5,7-dodecadienol, (E,E)-8,10-dodecadienol, (E,Z)-8,10-dodecadienol, (Z,Z)-8,10-dodecadienol, (Z,E)-8,10-dodecadienol, (E,Z)-7,9-dodecadienol, (Z,Z)-7,9-dodecadienol, (E)-5-tetradecenol, (Z)-8-tetradecenol, (Z)-9-tetradecenol, (E)-9-tetradecenol, (Z)-10-tetradecenol, (Z)-11-tetradecenol, (E)-11-tetradecenol, (Z)-11-hexadecenol, (Z,E)-9,11-tetradecadienol, (Z,E)-9,12-tetradecadienol, (Z,Z)-9,12-tetradecadienol, (Z,Z)-10,12-tetradecadienol, (Z,Z)-7,11-hexadecadienol, (Z,E)-7,11-hexadecadienol, (E)-14-methyl-8-hexadecen-1-ol, (Z)-14-methyl-8-hexadecen-1-ol, (E,E)-10,12-hexadecadienol, (E,Z)-10,12-hexadecadienol, dodecanal, (Z)-9-dodecanal, tetradecanal, (Z)-7-tetradecenal, (Z)-9-tetradecenal, (Z)-11-tetradecenal, (E)-11-tetradecenal, (E)-11,13-tetradecadienal, (E,E)-8,10-tetradecadienal, (Z,E)-9,11-tetradecadienal, (Z,E)-9,12-tetradecadienal, hexadecanal, (Z)-8-hexadecenal, (Z)-9-hexadecenal, (Z)-10-hexadecenal, (E)-10-hexadecenal, (Z)-11-hexadecenal, (E)-hexadecenal, (Z)-12-hexadecenal, (Z)-13-hexadecenal, (Z)-14-methyl-8-hexadecenal, (E)-14-methyl-8-hexadecenal, (Z,Z)-7,11-hexadecadienal, (Z,E)-7,11-hexadecadienal, (Z,E)-9,11-hexadecadienal, (E,E)-10,12-hexadecadienal, (E,Z)-10,12-hexadecadienal, (Z,E)-10,12-hexadecadienal, (Z,Z)-10,12-hexadecadienal, (Z,Z)-11,13-hexadecadienal, octadecenal, (Z)-11-octadecenal, (E)-13-octadecenal, (Z)-13-octadecenal, (Z)-5-decenyl 3-methylbutanoate and (+)cis-7,8-epoxy-2-methyloctadecane.

The pheromone is added to the formulation in the amount from about 0.01% to about 15%, preferably from about 0.1 to about 2.5%.

2. Insecticides

Additionally, the attractant of the invention is optionally combined with an insecticide which kills the insect lured to the trap, bait, or to the other types of formulations. The insecticides are generally carbamates, organophosphorous compounds, nitrophenols, nitromethylenes, phenylbenzoylureas, pyrethroids, chlorinated hydrocarbons and microbials (e.g., Bacillus thuringiensis), among others.

The following substances are examples of suitable insecticides: abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyfluthrin, bifenthrin, bioresmethrin, BPMC, brofenprox, bromophos A, bufencarb, buprofezin, butocarboxin, butylpyridaben, cadusafos, carbaryl, carbofuran, carbophenothion, carbosulfan, cartap, CGA 157

419, CGA 184699, chloethocarb, chlorethoxyfos, chlorfenvinphos, chlorfluazuron, chlormephos, chlorpyrifos, chlorpyrifos M, cis-Resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoat, oxamyl, oxydemethon M, oxydeprofos, parathion A, parathion M, permethrin, phenothrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, resmethrin, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralocytrin, tralomethrin, triarathen, triazophos, triazuron, trichlorfon, triflumuron, trimethacarb, transfluthrin vamidothion, XMC, xylylcarb, zetamethrin.

Insecticides are added to the attractant/pheromone mixture in an amount from about 0.1 to about 20. Preferred insecticides are pyrethroids added in the amount from about 1 to about 15%, and more specifically in about 5–10%.

3. Formulating Additives

Formulating additives which may optimally be added to the attractant containing formulations are all additives which are conventionally used in the production of plant treatment products and which are non-toxic to plants. The following additives are suitable to be added.

Non-ionic and anionic emulsifiers, such as polyoxyethylene fatty acid esters, polyoxyethylene fatty alcohol ethers and alkylaryl surfactants. Other suitable emulsifiers can be found in McCutcheon's *Emulsifiers and Detergents* (1982), North America Edit., MC Publishing Co., Glen Rock, N.J.

Antioxidants, such as sterically hindered phenols and alkyl-substituted hydroxyanisoles and hydroxytoluenes, PERMALUX®, NEOZONE® A or D, TOPANOL CA®, N,N'-diphenyl-1,4-phenylenediamine and other substituted phenylenediamines.

Thickeners, including organic polymers such as partially or fully neutralized polyacrylic acids, polyethylene glycols, polyvinyl alcohols and non-ionically or ionically modified celluloses, xanthan-based thixotropic thickeners, waxes and inorganic disperse thickeners, such as precipitated or pyrogenic silicas, kaolins, bentonites and aluminum/silicon mixed oxides.

Antifreeze agents, such as urea, glycerol or propylene glycol.

Fillers, such as rockmeals, calcium carbonate, quartzmeal and aluminum/silicon mixed oxides or mixed hydroxides.

Solvents such as glycols, such as propylene glycol and polyethylene glycols of different molecular weight; ketones, such as methyl isobutyl ketone, methyl isopropyl ketone and cyclohexanone; amides, such as dimethylformamide or diethylformamide; N,N-dialkylated carboxamides; alkyl lactams, such as substituted pyrrolidones and caprolactams hydrocarbons; n-paraffins and isoparaffins having different boiling ranges as they are obtainable, aromatic hydrocarbons, such as xylene and aromatic distillation fractions; esters, such as propylene glycol monomethyl ether acetate, dibutyl adipate and di-n-butyl phthalate; ethers, such as propylene glycol methyl ether or propylene glycol butyl ether; alcohols, such as ethanol, n- and i-propanol, n- and i-butanol, n- and i-amyl alcohol, benzyl alcohol, tetrahydrofurfuryl alcohol, 1-methoxy-2-propanol and higher alcohols, and dimethyl sulphoxide, dioxane and tetrahydrofuran. The solvents can be employed in the form of individual components or mixtures. Particularly preferred are those which are miscible with the UV stabilizers and which are not unduly volatile.

The additives, in general, may be added in concentrations from 0 to about 50%, by weight, preferably between about 0 and 25% and most preferably from 0.1% to about 5%.

Additionally, ultraviolet (UV) absorbers may be added. The UV absorbers may be liquid, solid or flowable and have preferably an absorption range from 270 to 400 nm. Representative UV absorbers are 2-H-benzotriazoles, 2-hydroxy-alkoxybenzophenones, oxalanilides, cinnamic acid and derivatives thereof, and triazines and derivatives thereof. UV absorbers are present generally in concentrations from about 1 to 50%, by weight, preferably between 5 to 30%, by weight.

UV blocking agents such as carbon black, iron oxide, titanium dioxide, zinc oxide, calcium carbonate, talc, etc., and dyestuffs, such as Sudan block, chromophthalic blue, Terasil blue and Cibacet yellow, may also be used.

D. Host Plant Volatile Blends

This invention is based on findings that adult insects and larvae of codling moth and other Lepidoptera are strongly attracted to host volatile odors from ripe pome fruits, particularly from ripe apples and pears and that such attraction is different from sex pheromones in that these attractants attract insects of both sexes as well as larvae and that these attractants cause larval aggregation or arrest. Unexpectedly, and surprisingly, these attractants are derived preferentially from ripe fruit, while it is a well known fact confirmed during development of the current invention that codling moths prefer to attack immature, nonripened apples and pears over English walnut. This strong preference for pears and apples over walnuts was studied by analyzing the odor composition of these fruits by GC-MS. Results were compared to odor composition of walnuts.

Odor analysis of host volatile odors of pome fruit specifically, apples and pears, identified a large number of volatile compounds present in these fruits, as described in section I-A. Of these compounds, several compounds present only in ripe pear and apple odor were found to be novel, specific and potent larval and adult female and male codling moth attractants.

These findings were unexpected and surprising because it is not obvious that attractants would be present in ripe fruit odor since ripe fruit is not normally attacked by the insect pest. The insect pest attacks immature, unripe fruit.

In order to determine whether it is an individual compound or a mixture of compounds which attract both the female and male codling moth, over 23 various blends of the volatile compounds (a total of 75 different compounds) found in the pome fruits were prepared and tested for male and female codling moth attractancy.

Studied synthetic blends of apple and pear volatiles were blends of aldehydes, alcohols, esters, monoterpenes and sesquiterpenes. The list of these blends is found in Table 2.

tion and development of odors from immature and ripe fruit odors of four apple varieties and of Bartlett pears.

The blends listed in Table 2 were then field tested in walnut orchards for their attractancy to male and female codling moths, and also for enhancement with synthetic codling moth pheromone and other additives identified above. Their total capture (both males and females), and

TABLE 2

Synthetic Blends of Apple and Pear Volatiles

Alcohol Blends

| | |
|---|---|
| Alcohol-1: 4- and 5-carbon Alcohols | (2-Methylpropan-1-ol, 2-Methylbutan-1-ol, 3-Methylbutan-1-ol) |
| Alcohol-2: 5-carbon Alcohols | (Petan-1-ol, Petan-2-ol) |
| Alcohol-3: 6-carbon Alcohols | (Hexan-1-ol, (E)-Hex-2-en-1-ol, Hex-3-en-ol, (E)-Hex-2-en-1-ol, (Z)-Hex-3-en-1-ol) |
| Alcohol-4: 7-, 8-, and 9-carbon Alcohols | (Heptan-1-ol, Octan-1-ol, Nonan-2-ol) |

Aldehyde Blends

| | |
|---|---|
| AL-1: 6-carbon Aldehydes | (Hexanal, (Z)-Hex-3-enal, (E)-Hex-2-enal) |
| AL-2: 9- and 10-carbon Aldehydes | (Nonanal, Decanal) |

Ester Blends

| | |
|---|---|
| Ester-1: 4-carbon Acetates | (Butyl acetate, 2-Methylpropyl acetate, Pentyl acetate, 2-Methylbutyl acetate, 3-Methylbutyl acetate) |
| Ester-2: 6-carbon Acetates | (Hexyl acetate, (E)-Hex-2-enyl acetate, (Z)-Hex-3-enyl acetate) |
| Ester-3: Propanoates | (Propyl propanoate, Hexyl propanoate, Butyl propanoate) |
| Ester-4: Butanoates | (Methyl butanoate, Ethyl butanoate, Propyl butanoate, Ethyl 2-methylbutyrate, Butyl 2-methylpropanoate, Butyl butanoate, Butyl 2-methylbutanoate, Hexyl butanoaic, Hexyl 2-methylbutanoate) |
| Ester-5: 7- and 8-carbon Acetates | (Heptyl acetate, Octyl acetate) |
| Ester-6: Hexanoates | (Methyl hexanoate, Ethyl hexanoate, Butyl hexanoate, Hexyl hexanoate) |
| Ester-7: "Apple Maggot Lure" | (Hexyl acetate, Butyl hexanoate, Hexyl butanoate, Propyl hexanoate, Butyl-2-methylbutyrate, Hexyl propanoate) |
| Ester-8: Octanoates | (Methyl octanoate, Ethyl octanoate) |
| Ester-10: Decanoates & Decadienoates | (Methyl decanoate, Ethyl decanoate, Methyl (2E,4Z)-2,4-decadienoate, Ethyl (2E,4Z)-2,4-decadienoate) |
| Ester-11: 2-Methylbutyl-esters | (2-Methylbutyl acetate, 2-Methylbutyl propanoate, 2-Methylbutyl butanoate, 2-Methylbutyl hexanoate) |
| Ester-12: 2-Methylpropyl-esters | (2-Methylpropyl acetate, 2-Methylpropyl propanoate, 2-Methylpropyl 2-methylbutyrate) |
| Ester-13: 4- and 6-Carbon Esters | (Butyl acetate, Hexyl acetate, Butyl butanoate, Hexyl butanoate, Butyl hexanoate, Hexyl-2-methylbutanoate, Hexyl hexanoate, 2-Methylbutyl acetate, Butyl 2-methylbutanoate) |
| Ester-14: 4:6-Carbon Esters | (Hexyl butanoate, Butyl hexanoate) |

Monoterpene Blends

| | |
|---|---|
| MT-1: (Pear/Apple-based) | (±-α-Pinene, ±-Linalool, Δ-3-Carene, (E)-β-Ocimene) |
| MT-2: (Walnut-based) | (γ-Terpinene, Terpinen-4-ol, ρ-Cymene, Myrcene, (E)-β-Ocimene, β-Pinene) |

Sesquiterpenes Blends

| | |
|---|---|
| ST-1: (Apple/Pear/Walnut-based) | (α-Farnesene, β-Caryophyllene, Germacrene d) |
| ST-2: (Pear) | (α-Copanene, δ-Cadiene, Humulene) |

Each component within the blends was present in an equal volume ratio.

The tested volatile compounds were selected on the basis of GC-MS analyses of headspace trappings of the maturatheir individual male and female capture were determined and results obtained, were compared to insect capture obtained with purified individual ester, compound #25 namely ethyl (2E,4Z)-2,4-decadienoate, and to the codling moth male sex pheromone compound #26 in Table 3. Results are seen in Table 3.

TABLE 3

| # | Host Plant Volatile (HPV) Blends | Total CM Captured with HPV: (CM/trap/ night ± SEM | MALE CM Captured with HPV; ♂♂/trap/ night ± SEM | FEMALE CM Captured with HPV; ♀♀/trap night ± SEM | Biological Significance |
|---|---|---|---|---|---|
| 1 | Aldehyde Blend #1, "AL-1" | 0 | 0 | 0 | Non-attractive |
| 2 | Aldehyde Blend #2, "AL-2" | 0 | 0 | 0 | Non-attractive |
| 3 | Alcohol Blend #1, "OL-1" | 0 | 0 | 0 | Non-attractive |
| 4 | Alcohol Blend #2, "OL-2" | 0 | 0 | 0 | Non-attractive |
| 5 | Alcohol Blend #3, "OL-3" | 0 | 0 | 0 | Non-attractive |
| 6 | Alcohol Blend #4, "OL-4" | 0 | 0 | 0 | Non-attractive |
| 7 | Ester Blend #1, "Est-1" | 0 | 0 | 0 | Non-attractive |
| 8 | Ester Blend #2, "Est-2" | 0 | 0 | 0 | Non-attractive |
| 9 | Ester Blend #3, "Est-3" | 0 | 0 | 0 | Non-attractive |
| 10 | Ester Blend #4, "Est-4" | 0 | 0 | 0 | Non-attractive |
| 11 | Ester Blend #5, "Est-5" | 0 | 0 | 0 | Non-attractive |
| 12 | Ester Blend #6, "Est-6" | 0 | 0 | 0 | Non-attractive |
| 13 | Ester Blend #7, "Est-7" | 0 | 0 | 0 | Non-attractive |
| 14 | Ester Blend #8, "Est-8" | 0 | 0 | 0 | Non-attractive |
| 15 | Ester Blend #10, (10 mg) "Est-10" | 2.20 ± 1.36 | 0.88 ± 0.54 | 1.32 ± 0.82 | Bisexual Attractant |
| 16 | Ester Blend #11, "Est-11" | 0 | 0 | 0 | Non-attractive |
| 17 | Ester Blend #12, "Est-12" | 0 | 0 | 0 | Non-attractive |
| 18 | Ester Blend #13, "Est-13" | 0 | 0 | 0 | Non-attractive |
| 19 | Ester Blend #14, "Est-14" | 0 | 0 | 0 | Non-attractive |
| 20 | Monoterpene Blend #1, "MT-1" | 0 | 0 | 0 | Non-attractive |
| 21 | Monoterpene Blend #2, "MT-2" | 0 | 0 | 0 | Non-attractive |
| 22 | Sesquiterpene Blend #1, "ST-1" | 0 | 0 | 0 | Non-attractive |
| 23 | Sesquiterpene Blend #2, "ST-2" | 0 | 0 | 0 | Non attractive |
| 24 | Solvent Controls | 0 | 0 | 0 | Non-attractive |
| 25 | Ethyl (2E,4Z)-2,4-Decadienoate (5 mg) | 3.46 ± 1.44 | 1.42 ± 0.59 | 2.04 ± 0.85 | Bisexual Attractant |
| 26 | Codling Moth Pheromone Standard | 3.15 ± 0.98 | 3.15 ± 0.98 | 0.0 | MALE Attractant |

Table 3 shows attraction of the codling moth to host plant volatile blends of various groups of compounds previously identified in apple or pear odors. Individual blends containing representative aldehyde, alcohol, ester, monoterpene or sesquiterpene blends were provided in the traps in 10 mg/white septa.

Individual host-plant volatile (HPV) blends identified by the #1–23 in Table 3 were tested for codling moth attractancy in a walnut orchard, and the results were compared to the isolated purified ethyl (2E,4Z)-2,4-decadienoate (#25), to pheromone (#26) and to solvent controls (#24).

As seen from Table 3, in this study the blend #15, i.e., ester blend #10 (10 mg) containing synthetic pear extracts, and purified ethyl (2E,4Z)-2,4-decadienoate (5 mg) resulted in the capture of both male and female codling moths and are therefore effective bisexual attractants.

Ethyl (2E,4Z)-2,4-decadienoate (#25) was the most effective and superior bisexual attractant, and is, therefore, preferred as an individual compound. Ester blend #10 was found to be the most active bisexual attractant blend and is, therefore, most preferred as the blend. This blend elicited strong codling moth attraction of primarily females (1.32 moths/night) over males (0.88 moths/night) in mid-season. The ester blend #10 was thus identified as a bisexual attractant, attracting more females (60–80%) than males. However, as seen from Table 3, this blend's activity (2.20 moths/night at 10 mg) was only about two thirds of that of the individual purified compound #25 (3.46 moths/night at 5 mg) in this test.

The ester blend #10 was then tested for male and female flight patterns and results were compared to male flight pattern in response to sex pheromone. Results show that the female flight pattern response to the ester blend #10 was similar to the male flight pattern response to sex pheromones, but slightly shifted in phase. Results are shown in FIGS. 1 and 2.

FIG. 1 illustrates attraction of female and male codling moths to the ester blend #10 baited sticky trap. As seen in FIG. 1, both males and females were attracted to the ester blend #10 confirming that the blend had bisexual attractancy.

Figure 2:
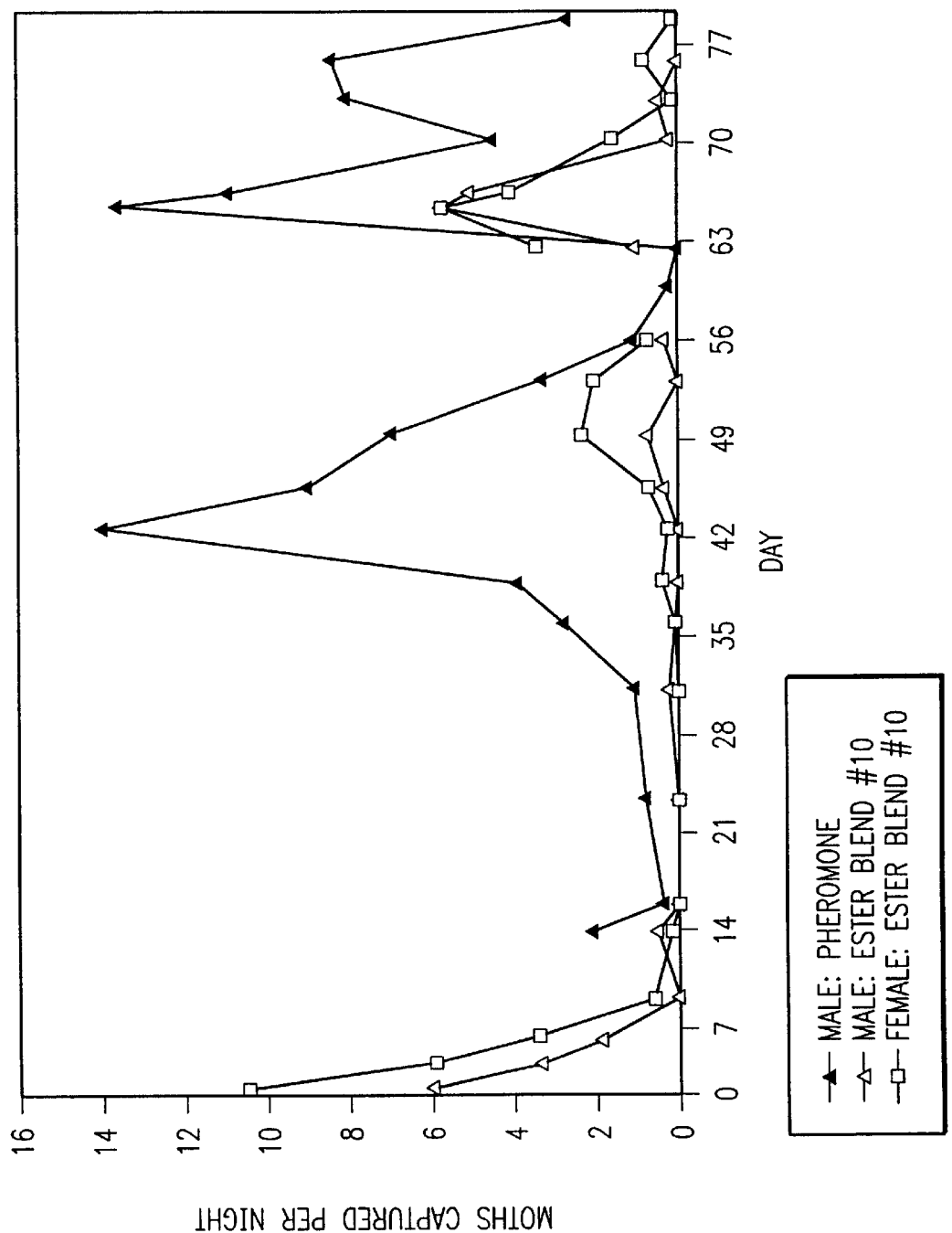
FIG. 2 is a graph comparing the codling moth flight pattern delineated by males captured in pheromone traps (-▲-) to the flight pattern of both sexes captured in synthetic pear extract blend containing traps. Male codling moth (-Δ-), female codling moth (-□-) capture in ester blend #10-baited traps.

FIG. 2 illustrates and compares flight pattern delineated by males captured in pheromone trap (-▲-), versus both sexes, i.e. males (-△-) and females (-□-), captured in HPV ester blend #10 baited trap. As seen in FIG. 2, the ester blend #10 was able to elicit similar flight pattern in codling moth females as that elicited in males by the male sex pheromone.

A single compound ethyl (2E,4Z)-2,4-decadienoate present in HPV ester blend #10 was found most attractive, especially to female codling moths.

Since it was a single ester compound which showed the highest bisexual attraction of codling moth, an additional study was performed with individual compounds, typically of purity 90–98%, including alcohols, such as (E)-2-decen-1-ol, (Z)-4-decen-1-ol, 9-decen-1-ol, 2,4-decadien-1-ol, and 2,4-dodecadien-1-ol; aldehydes, such as (E)-2-decenal, (E)-4-decenal, (Z)-4-decenal, 2,4-decadienal and (E,Z)-2,6-decadienal; and esters, such as (E)-2-decen-1-yl acetate, 9-decen-1-yl acetate, ethyl sorbate, ethyl (E)-2-decenoate, ethyl (E)-4-decenoate, methyl (2E,4Z)-2,4-decadienoate and ethyl (2E,4Z)-2,4-decadienoate. Attractive activity of these compounds for male and female codling moth was compared to purified ethyl (2E,4Z)-2,4-decadienoate.

When the cumulative evaluation of all studied compounds and/or blends containing aldehyde, alcohol, ester and terpene compounds was made, the following results clearly confirmed the findings seen in Table 3. Alcohol odors from pears possessed no attractancy for females and only one studied alcohol, namely (2,4)-2,4-decadien-1-ol, showed only very low male attractancy. Aldehydes were found to be non-attractive to both sexes. Pear or apple derived odorous esters, on the other hand, were found to be bisexually attractive to codling moth, albeit, some were more attractive than others.

These esters were active, selective and specific bisexual attractants for codling moth and other species of Lepidoptera. The most active and therefore preferred ester attractants are purified ethyl (2E,4Z)-2,4-decadienoate, methyl (2E,4Z)-2,4-decadienoate, ethyl (2E)-2-decenoate and (E)-2-decen-1-yl acetate and isomers thereof.

E. Individual Synthetic Pure Esters and Isomers Thereof

Because the esters in the ester blend #10 were found to be effective bisexual attractants, the attraction of codling moth to (2E,4E) and (2E,4Z) isomers of 2,4-decadienoic acid esters with various chain-length alcohol moieties was studied. In this study, test compounds were highly purified synthetic samples. The purities of the compounds are expressed as percentages. Individual traps were baited with 1 mg dose/gray septum; five replicate blocks in four orchards; means of 21 total trap checks.

Results are seen in Table 4.

TABLE 4

| Ester of (2E,4Z) and (2E,4E) Isomers of 2,4-Decadienoic Acid: | Total CM Captured: CM/trap/ night ± SEM | MALE CM Captured: ♂♂/trap/ night ± SEM | FEMALE CM Captured: ♂♂/trap/ night ± SEM | Biological Significance: |
|---|---|---|---|---|
| Synthetic Pure Esters | | | | |
| Methyl (2E,4E)-2,4-Decadienoate (100%) | 0.05 ± 0.03 | 0.01 ± 0.01 | 0.04 ± 0.03 | Very low Attraction |
| Methyl (2E,4Z)-2,4-Decadienoate (98.3%) | 0.54 ± 0.19 | 0.12 ± 0.07 | 0.41 ± 0.14 | Low Attraction |
| Ethyl (2E,4E)-2,4-Decadienoate (99.5%) | 0.77 ± 0.20 | 0.24 ± 0.06 | 0.52 ± 0.23 | Low Attraction |
| Ethyl (2E,4Z)-2,4-Decadienoate, #1 (95.3%) | 4.49 ± 1.29 | 1.67 ± 0.41 | 2.82 ± 0.89 | High Attraction |
| Ethyl (2E,4Z)-2,4-Decadienoate, #2 (88.5%) | 4.25 ± 1.43 | 1.89 ± 0.79 | 3.14 ± 1.15 | High Attraction |
| n-Propyl (2E,4E)-2,4-Decadienoate (98.5%) | 0.36 ± 0.19 | 0.17 ± 0.13 | 0.19 ± 0.07 | Low Attraction |
| n-Propyl (2E,4Z)-2,4-Decadienoate (96.5%) | 1.61 ± 0.49 | 0.49 ± 0.14 | 1.12 ± 0.39 | Moderate Attraction |
| Isopropyl (2E,4E)-2,4-Decadienoate (99.2%) | 0.14 ± 0.05 | 0.05 ± 0.02 | 0.09 ± 0.04 | Very Low Attraction |
| Butyl (2E,4E)-2,4-Decadienoate (99.2%) | 0.02 ± 0.02 | 0.02 ± 0.02 | 0 | Very Low Attraction |
| Hexyl (2E,4Z)-2,4-Decadienoate (100%) | 0.02 ± 0.02 | 0.01 ± 0.01 | 0.02 | Very Low Attraction |
| Hexyl (2E,4Z)-2,4-Decadienoate (91.6%) | 0.57 ± 0.22 | 0.21 ± 0.09 | 0.36 ± 0.18 | Low Attraction |
| Ester Blend #10 (94.6%) | 2.25 ± 0.60 | 0.84 ± 0.38 | 1.41 ± 0.38 | High Attraction |
| Standards | | | | |
| Pheromone (E,E)-8,10-Dodecadienol | 7.13 ± 1.94 | 7.13 ± 1.94 | 0 | Male only Attraction |
| Solvent Control | 0.03 ± 0.03 | 0 | 0.03 ± 0.03 | Very low Attraction |

As seen in Table 4, purified esters have shown variable degree of attraction of codling moth, ranging from no attractancy or very low, to high bisexual attractancy. Even when only very low attractancy is observed, such attractancy is in all but one case higher for females than males. Moreover, the esters attractancy is different between geometrical isomers of these esters as seen in Table 4. Table 4 clearly illustrates that the (2E,4Z)-isomers possess more attractancy for codling moth than their corresponding (2E, 4E)-isomers.

Additionally, studies were performed to determine the attraction of codling moth to proportional mixes of (2E,4Z) and (2E,4E) isomers of ethyl 2,4-decadienoate and highly purified samples of each. The results are seen in Table 5. Traps were baited with 1 mg dose/gray septum.

TABLE 5

| Mixtures of Isomers of Ethyl 2,4-Decadienoate: "2E,4Z: 2E,4E" (vol:vol) [calculated actual isomer content 2E, 4Z%, 2E, 4E%] | Total CM Captured: CM/trap ± SEM | Male CM Captured: ♂♂/trap/night ± SEM | Female CM Captured ♀♀/trap/night ± SEM | Biological Significance |
|---|---|---|---|---|
| Ethyl (2E,4Z)-2,4-Decadienoate [95.32%, 1.75%] | 1.38 ± 0.37 | 0.62 ± 0.29 | 0.76 ± 0.10 | Best Attraction |

TABLE 5-continued

| Mixtures of Isomers of Ethyl 2,4-Decadienoate: "2E,4Z: 2E,4E" (vol:vol) [calculated actual isomer content 2E, 4Z%, 2E, 4E%] | Total CM Captured: CM/trap ± SEM | Male CM Captured: ♂♂/trap/night ± SEM | Female CM Captured ♀♀/trap/night ± SEM | Biological Significance |
|---|---|---|---|---|
| "95:5" [90.6%, 6.7%] | 1.19 ± 0.39 | 0.29 ± 0.08 | 0.91 ± 0.31 | Good Attraction |
| "80:20" [76.3%, 21.3%] | 0.85 ± 0.36 | 0.43 ± 0.25 | 0.43 ± 0.22 | Fair Attraction |
| "50:50" [47.8%, 50.8%] | 0.95 ± 0.34 | 0.62 ± 0.25 | 0.33 ± 0.10 | Fair Attraction |
| "20:80" [19.3%, 80.1%] | 0.95 ± 0.41 | 0.57 ± 0.22 | 0.38 ± 0.21 | Fair Attraction |
| "5:95" [5.0%, 94.8%] | 0.29 ± 0.14 | 0.05 ± 0.05 | 0.24 ± 0.14 | Low Attraction |
| Ethyl (2E,4E)-2,4-Decadienoate [0.28%, 99.72%] | 0.24 ± 0.10 | 0.19 ± 0.05 | 0.05 ± 0.05 | Low Attraction |

As seen in Table 5, both isomers of ethyl 2,4-decadienoate in mixtures provided good attraction of codling moth. The degree of the attraction, however, depended on percentile representation of the 2E,4Z isomer rather than the 2E,4E isomer.

F. Interactive Effect of Attractants and Pheromones

When the mixtures of the attractant with pheromone were studied and capture of male and female codling moths analyzed, the number and proportion of captured males vs. females clearly depended on the presence and amount of pheromone.

Results are seen in Table 6.

TABLE 6

| | | Combined Mean Data CM/trap/night | | |
|---|---|---|---|---|
| Dose Attract-ant | Dose Phero-mone | Total CM Captured (6 reps) ± SEM | Male CM Captured: (6 reps) ± SEM | Female CM Captured (6 reps) ± SEM |
| 1.0 mg | 1.0 mg | 1.94 ± 0.29 | 1.30 ± 0.30 | 0.64 ± 0.13 |
| 0.1 mg | 1.0 mg | 2.98 ± 0.87 | 2.43 ± 0.72 | 0.55 ± 0.16 |
| 10 ug | 1.0 mg | 2.92 ± 0.57 | 2.78 ± 0.54 | 0.15 ± 0.07 |
| 1 ug | 1.0 mg | 1.46 ± 0.22 | 0.85 ± 0.22 | 0.60 ± 0.10 |
| 0.1 mg | 0.1 mg | 2.71 ± 0.81 | 1.92 ± 0.73 | 0.79 ± 0.24 |
| 10 ug | 0.1 mg | 1.91 ± 0.98 | 2.81 ± 0.97 | 0.10 ± 0.05 |
| 1 ug | 0.1 mg | 2.94 ± 0.59 | 2.89 ± 0.62 | 0.05 ± 0.03 |
| 1.0 mg | 10 ug | 1.15 ± 0.33 | 0.60 ± 0.20 | 0.56 ± 0.15 |
| 0.1 mg | 10 ug | 1.13 ± 0.19 | 0.62 ± 0.18 | 0.51 ± 0.14 |
| 10 ug | 10 ug | 1.31 ± 0.57 | 1.19 ± 0.51 | 0.12 ± 0.07 |
| 1 ug | 10 ug | 0.87 ± 0.19 | 0.85 ± 0.20 | 0.02 ± 0.02 |
| 1.0 mg | 1 ug | 1.65 ± 0.38 | 0.38 ± 0.10 | 1.27 ± 0.28 |
| 0.1 mg | 1 ug | 0.74 ± 0.23 | 0.17 ± 0.08 | 0.57 ± 0.16 |
| 10 ug | 1 ug | 0.25 ± 0.09 | 0.19 ± 0.10 | 0.05 ± 0.03 |
| 1 ug | 1 ug | 0.66 ± 0.50 | 0.63 ± 0.47 | 0.02 ± 0.02 |

As seen in Table 6, the capture of total codling moths clearly depended on interaction of the attractant ethyl (2E, 4Z)-2,4-decadienoate with the specific codling moth pheromone (E,E)-8,10-dodecadien-1-ol. For the study seen in Table 6, both compounds were loaded on separate septa in concentrations as seen in the Table 6, and placed in the same traps in three replicate orchard blocks. Results are shown as mean catch per night.

The data clearly show that with higher doses of pheromone, more males are captured. When the dose of pheromone is decreased, the ratio of captured females increases, see, for example, the mix of 1 mg of attractant and 1 $\mu$g of pheromone where the total mean capture of moths is 1.7 of which 1.3 are females. The attractant in combination with the pheromone thus shows additive or co-active attraction enhancement effects.

Interaction of synthetic apple and pear odor blends, described above in Table 2, and their effect on the attractancy of synthetic pheromone to codling moth was also studied. For that purpose, series of paired-traps containing pheromone alone or pheromone in combination with synthetic host plant volatile blends were placed in walnut orchards.

Results of this study are seen in Table 7, which shows mean catch per trap per night.

TABLE 7

| | Host Plant Volatile (HPV) Blend or Extract: | Male CM Capture with Pheromone Alone Trap: ± SEM | Male CM Capture with Pheromone + HPV Blend: ± SEM | % Change (PH + HPV/ PH × 100) in Male Capture: | HPV Blend Impact on Pheromone Attractancy to Male CM |
|---|---|---|---|---|---|
| 1 | Apple Extract, "Ap-Ext" | 1.87 ± 0.75 | 1.40 ± 0.62 | 75% | No Effect |
| 2 | Aldehyde Blend #1, "AL-1" | 1.67 ± 0.68 | 2.07 ± 0.90 | 124% | Low Effect |
| 3 | Aldehyde Blend #2, "AL-2" | 1.53 ± 0.60 | 0.53 ± 0.22 | 35% | Inhibition |
| 4 | Alcohol Blend #1, "OL-1" | 1.93 ± 0.80 | 2.47 ± 1.01 | 128% | Low Effect |
| 5 | Alcohol Blend #2, "OL-1" | 1.80 ± 0.72 | 0.60 ± 0.24 | 33% | Inhibition |
| 6 | Alcohol Blend #3, "OL-3" | 1.13 ± 0.50 | 0.87 ± 0.43 | 77% | No Effect |
| 7 | Alcohol Blend #4, "OL-4" | 0.20 ± 0.12 | 0.20 ± 0.12 | 100% | No Effect |

TABLE 7-continued

| Host Plant Volatile (HPV) Blend or Extract: | Male CM Capture with Pheromone Alone Trap: ± SEM | Male CM Capture with Pheromone + HPV Blend: ± SEM | % Change (PH + HPV/ PH × 100) in Male Capture: | HPV Blend Impact on Pheromone Attractancy to Male CM |
|---|---|---|---|---|
| 8 Ester Blend #1, "Est-1" | 3.60 ± 1.39 | 2.00 ± 0.89 | 56% | Inhibition |
| 9 Ester Blend #2, "Est-2" | 3.60 ± 1.77 | 0.93 ± 0.41 | 26% | Inhibition |
| 10 Ester Blend #3, "Est-3" | 0.73 ± 0.37 | 0.80 ± 0.37 | 110% | No effect |
| 11 Ester Blend #4, "Est-4" | 2.13 ± 0.98 | 0.60 ± 0.24 | 28% | Inhibition |
| 12 Ester Blend #5, "Est-5" | 2.80 ± 1.17 | 2.40 ± 0.94 | 86% | No effect |
| 13 Ester Blend #6, "Est-6" | 1.06 ± 0.41 | 1.00 ± 0.39 | 94% | No effect |
| 14 Ester Blend #7, "Est-7" | 4.93 ± 2.03 | 3.40 ± 1.44 | 69% | No effect |
| 15 Ester Blend #8, "Est-8" | 3.00 ± 1.23 | 1.33 ± 0.54 | 44% | Inhibition |
| 16 Ester Blend #10, "Est-10" | 1.53 ± 0.68 | 3.22 ± 0.89 | 211% | Attraction Enhancement |
| 17 Ester Blend #11, "Est-11" | 1.00 ± 0.42 | 0.80 ± 0.41 | 80% | No Effect |
| 18 Ester Blend #12, "Est-12" | 1.00 ± 0.45 | 0.53 ± 0.22 | 53% | Inhibition |
| 19 Ester Blend #13, "Est-13" | 4.20 ± 1.61 | 2.53 ± 1.03 | 60% | Inhibition |
| 20 Ester Blend #14, "Est-14" | 3.47 ± 14.2 | 4.27 ± 1.62 | 123% | Low Effect |
| 21 Monoterpene Blend #1, "MT-1" | 1.53 ± 0.64 | 1.47 ± 0.58 | 96% | No Effect |
| 22 Monoterpene Blend #2, "MT-2" | 4.00 ± 1.61 | 4.87 ± 1.87 | 122% | Low Effect |
| 23 Sesquiterpene Blend #1, "ST-1" | 1.07 ± 0.44 | 1.13 ± 0.50 | 106% | No Effect |
| 24 Sequiterpene Blend #2, "ST-2" | 1.20 ± 0.58 | 1.67 ± 0.73 | 139% | Low Effect |
| 25 Solvent Control vs. Solvent Control | 1.02 ± 0.23 | 1.21 ± 0.27 | 119% | No Effect |

Results seen in Table 7 show that the combination of pheromone with the attractant of the invention or HPV ester blend #10 has significant enhancement effects on attraction vs. pheromone alone. However, all of the 23 other blends, when combined with pheromone have, in most instances, no effect. In some instances, there is a low or moderate effect, and in eight instances, there is an inhibitory effect.

Interaction of individual synthetic host plant volatiles or blends on the attractiveness of synthetic male pheromone to male codling moth administered in paired traps with pheromone alone or with pheromone and attractant 10 mg/red septum was also studied. Results are seen in Tables 8 and 9.

TABLE 8

| Host Plant Volatile (HPV) Individual Compounds and HPV Blends: | Male CM Captured, ♂♂/trap/night Orchard #1 | | Male CM Captured, ♂♂/trap/night Orchard #2 | | Male CM Captured, ♂♂/trap/night Orchard #3 | | Male CM Captured, ♂♂/trap/night Orchard #4 | | Average % Change in ♂♂ CM Capture |
|---|---|---|---|---|---|---|---|---|---|
| | Pheromone Alone Trap: ± SEM | HPV + Pheromone Trap: ± SEM | Pheromone Alone Trap: ± SEM | HPV + Pheromone Trap ± SEM | Pheromone Alone Trap: ± SEM | HPV + Pheromone Trap: ± SEM | Pheromone Alone Trap: ± SEM | HPV + Pheromone Trap: ± SEM | |
| Butan-1-ol | 0.73 ± 0.15 | 0.74 ± 0.17 101% | 2.34 ± 0.50 | 2.73 ± 0.56 117% | 2.41 ± 0.42 | 2.95 ± 0.43 122% | 3.10 ± 0.63 | 2.96 ± 0.62 96% | 109% |
| 3-Methyl Butan-1-ol | 1.09 ± 0.27 | 1.29 ± 0.25 118% | 1.38 ± 0.28 | 1.19 ± 0.22 86% | 2.98 ± 0.49 | 2.82 ± 0.56 95% | 2.51 ± 0.45 | 2.91 ± 0.49 115% | 104% |
| (E)-β-Ocimene | 1.04 ± 0.21 | 1.40 ± 0.25 135% | 0.77 ± 0.18 | 0.88 ± 0.17 114% | 2.33 ± 0.41 | 2.38 ± 0.34 102% | 3.09 ± 0.63 | 2.96 ± 0.62 96% | 112% |
| para-Cymene | 0.79 ± 0.15 | 0.92 ± 0.20 117% | 1.37 ± 0.32 | 1.39 ± 0.38 102% | 4.40 ± 0.87 | 4.76 ± 0.82 108% | 3.15 ± 0.49 | 4.27 ± 0.71 136% | 116% |
| β-Pinene | 1.24 ± 0.52 | 0.75 ± 0.50 61% | 2.00 ± 0.57 | 1.25 ± 0.29 63% | 2.60 ± 0.38 | 3.37 ± 0.53 130% | 4.41 ± 0.94 | 4.95 ± 0.76 112% | 92% |
| Ester Blend #10 | 0.72 ± 0.13 | 1.29 ± 0.31 179% | 0.77 ± 0.18 | 1.37 ± 0.22 178% | 3.82 ± 0.42 | 5.56 ± 0.69 146% | 1.54 ± 0.30 | 3.17 ± 0.64 206% | 177% |

TABLE 9

| Host Plant Volatile (HPV Extract, Blends and Compounds: | Male CM Capture with Pheromone Alone Trap: ♂♂/trap/night ± SEM | Male CM Capture with Pheromone + HPV Blend: ♂♂/trap/night ± SEM | % Change (Ph+HPV/Phxl 00) in Male CM Capture | Impact of HPV Blend on Pheromone Attractancy to Male CM |
|---|---|---|---|---|
| Apple Extract, "AP-Ext" | 0.92 ± 0.31 | 1.50 ± 0.33 | 163% | Good Effect |
| Alcohol Blend #1, "OL-1" | 0.92 ± 0.20 | 1.04 ± 0.22 | 113% | No Effect |
| Alcohol Blend #3, "OL-3" | 0.98 ± 0.49 | 0.74 ± 0.37 | 76% | No Effect |
| Ester Blend #1, "Est-1" | 1.05 ± 0.34 | 1.49 ± 0.39 | 142% | Good Effect |
| Ester Blend #2, "Est-2" | 1.04 ± 0.33 | 0.55 ± 0.20 | 53% | Inhibition |
| Ester Blend #7, "Est-7" | 1.28 ± 0.37 | 0.95 ± 0.41 | 74% | No Effect |
| Ester Blend #10, "Est-10" | 0.69 ± 0.25 | 1.80 ± 0.93 | 261% | Strong Enhancement |
| Ester Blend #14, "Est-14" | 0.93 ± 0.29 | 0.67 ± 0.29 | 72% | No Effect |
| Monoterpene Blend #2, "MT-2" | 1.04 ± 0.26 | 1.43 ± 0.28 | 138% | Good Effect |
| Myrcene | 1.22 ± 0.36 | 1.03 ± 0.26 | 84% | No Effect |
| gamma-Terpinene | 0.95 ± 0.28 | 0.88 ± 0.28 | 93% | No Effect |
| Sesquiterpene Blend #1, "ST-1" | 1.17 ± 0.28 | 0.97 ± 0.45 | 83% | No Effect |
| alpha-Farnesene | 1.61 ± 0.34 | 1.38 ± 0.39 | 86% | No Effect |
| Germacrene-D | 0.79 ± 0.17 | 0.86 ± 0.19 | 109% | No Effect |
| Solvent Control vs. Solvent Control | 1.04 ± 0.26 | 1.03 ± 0.38 | 99% | No Effect |

G. Enhancement of Pheromone Attractancy by Ester Blend #10

The ability of the HPV ester blend #10 to influence the pheromone attractancy/preference of codling moth was resolved using paired-traps, one trap with a pheromone septum alone and the other trap with a pheromone septum and an ester blend #10 septum. When co-evaporated with pheromone, ester blend #10 elicited a significantly greater rate of codling moth attraction/capture over that of the paired pheromone-alone trap. Results are seen in Tables 10 and 11, and FIG. 3.

This increase in codling moth pheromone trap capture was due in part to the additional capture of female moths that were lured to the ester blend #10, as female codling moths were shown not to be attracted by pheromone. The male codling moth responses support mixed interpretations between the 13 replications of these paired-trap tests.

Figure 3:
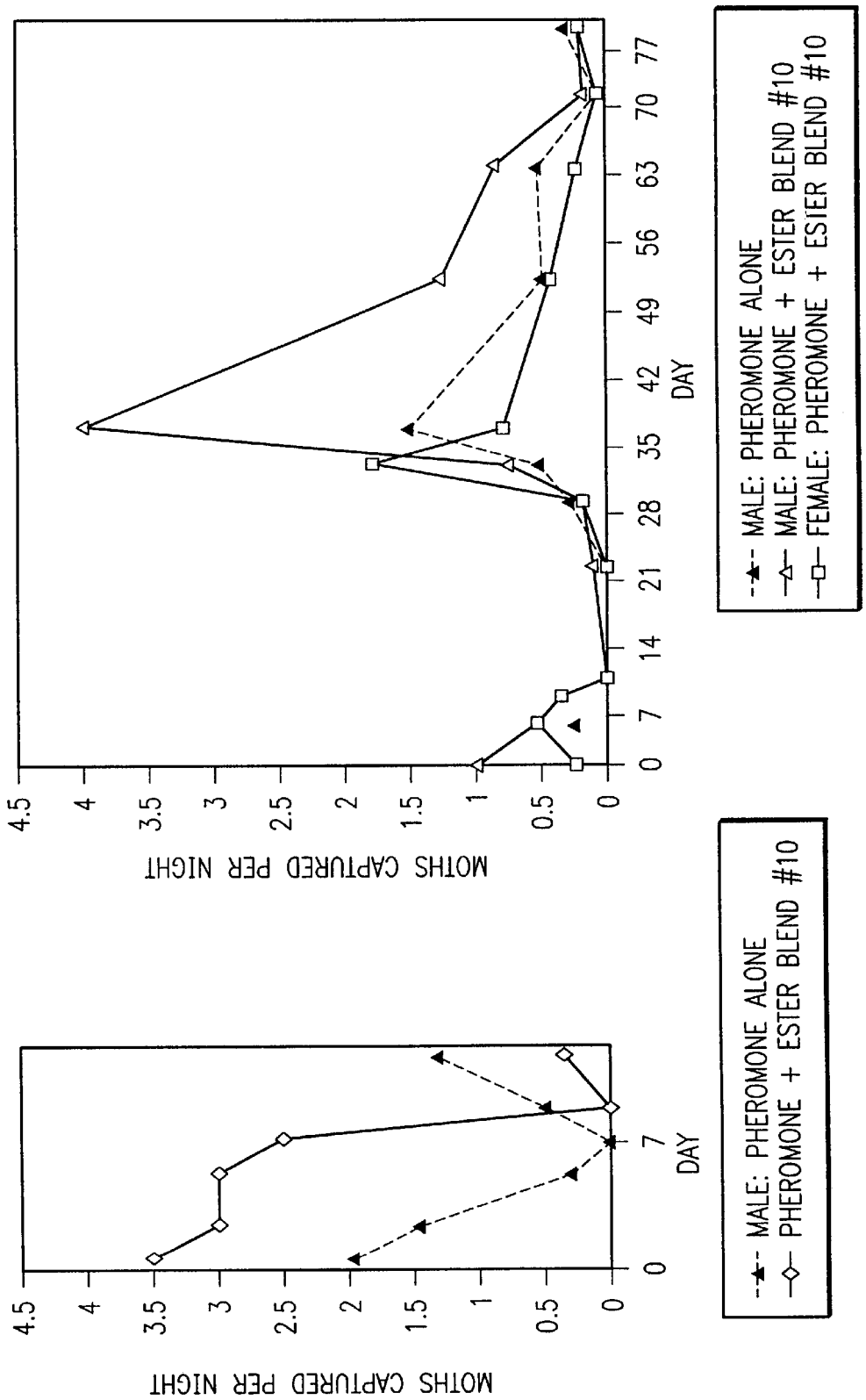
FIG. 3 are graphs of the enhancement of pheromone by a pear extract blend showing preference-attraction of codling moth in a paired-trap choice design, consisting of a trap baited with pheromone alone versus the trap baited with pheromone and a pear extract blend (ester blend #10). Male capture with pheromone alone (-▲-), codling moth (unsexed) capture with pheromone and pear extract blend (-●-), male capture with male pheromone and pear extract blend (-Δ-), female capture with male pheromone and pear extract blend (-□-).

For a set of replicated data, ester blend #10 significantly increased the number of male codling moths captured in the HPV-augmented pheromone trap (Table 10 and FIG. 3). HPV ester blend #10, therefore, acted as a pheromone enhancer. For certain other replications of these paired-trapping, the significant increase in the total number of captured codling moth, as seen in Table 11, appeared to be due to the co-active attractancy of the ester blend #10 to both sexes and not attributable to enhancement of male attraction to pheromone. Thus, it is unclear whether HPV ester blend #10 enhances pheromone attraction for codling moth males, but clearly this pear-derived odor does attract males and females to traps that co-emit pheromone, and thereby is a co-active attractant.

TABLE 10

| Moths/Night: | Male: PH Alone | Male: PH + Ester Blend #10 | Female: PH + Ester Blend #10 |
|---|---|---|---|
| Mean ± SEM | 0.55 ± 0.14 | 1.02 ± 0.27 | 0.42 ± 0.11 |
| Total Moths Caught: | 46 | 74 | 30 |
| T-Test ♂♂: PH + HPV | <0.05 | | |
| T-Test ♂♂ vs. ♀♀ | <0.05 | | |

PH = pheromone

Table 10 illustrates interaction of pheromone with HPV ester blend #10 on codling moth attraction, when tested in a conventional low-population Hartley walnut orchard. There were 13 traps and 18 trap check dates.

TABLE 11

| | Test 1 (2 Reps, trap checks) | | Test 2 (2 Reps, 50 trap checks) | |
|---|---|---|---|---|
| Moths/Trap/Night: | PH Alone | PH + Ester Blend #10 | PH Alone | PH + Ester Blend #10 |
| Mean ± SEM | 0.74 ± 0.13 | 1.13 ± 0.23 | 2.54 ± 0.43 | 4.1 ± 0.58 |
| Total Moths Caught: | 212 | 329 | 745 | 1120 |
| T-Test (PH vs. PH + HPV) | <0.001 | | <0.001 | |
| Sex Ratio ♂♂:♀♀ | 1:0.04 | 1:0.55 | 1:0.02 | 1:0.73 |

PH = pheromone

Table 11 illustrates interaction of pheromone (PH) and ester blend #10 on codling moth attraction. Results show mean capture of codling moths in paired traps: pheromone alone vs. pheromone and HPV ester blend #10 in a conventional low-population and an organic high-population Hartley walnut orchards.

FIG. 3 shows preference attraction of codling moths in a paired-trap choice design, consisting of a trap baited with pheromone alone or one baited with pheromone and HPV ester blend #10.

As seen in FIG. 3, the HPV ester blend #10, in combination with pheromone, achieved the largest capture of insects.

The fact that female codling moths are attracted to HPV ester blend #10 in the presence of high, localized emission levels of pheromone confirms an important beneficial effect of HPV ester blend #10. Thus, this HPV-based female-attractant is effective for monitoring codling moth population levels and flight patterns in orchards being treated with mating disruption formulations containing pheromone.

As seen in Tables 6–9, some of the synthetic pear or apple extract show low, good or excellent attraction for codling moth and, upon combination with male sex pheromone, enhancement effects on codling moth capture. Such enhancement effects result in higher capture of males. Overall, the addition of pheromone to the pear or apple host plant volatile attractant enhances the attractancy of the apple or pear extract volatile and thus results in increased effectiveness of insect capture.

H. Effect of Purity on the Attractant Activity

As has been shown above, the individual compounds isolated and purified by methods described in Examples, were shown to be more active than blends of purified or unpurified compounds and also more effective than commercially available individual unpurified compounds.

Additional purification procedures were conducted to show the differences and superiority of purified pear and apple volatiles over commercially available products. For that purpose, extracts were purified from commercially available compounds, typically available in only about 80–85% purity, to a purity between 90–100%, preferably over 98% purity. As the purity of the sample of ethyl (2E,4Z)-2,4-decadienoate increased so also did its attractancy to codling moths. For example, the mean captures (±SEM) were 4.5 (±2.0) for an 86% pure sample, 6.5 (±4.4) for a 93.6% pure sample and 9.3 (±3.2) for 98.8% pure sample.

Although non-purified commercially available compounds show good attractancy for both male and female insect, such attractancy may be further increased by purifying the attractants to over 90% up to 100% purity.

II. A Method for Attracting Insect Pest

The method for attracting insect pests comprises providing the attractant of the invention in baits, lures, sprays, films or traps suitable for monitoring, annihilation, mass trapping, disruption of mating behavior and overall control of insect pest population and reproduction.

A. Insects Responsive to the Attractants of the Invention

Generally, the method of the invention comprises attracting and luring the insect to the lure, baits, trap, formulation, etc., where the attractant of the invention is deposited alone or in admixture with other compounds. The method is most suitable for adult male and female and larvae of codling moth and other species of Lepidoptera.

Examples from the order Lepidoptera that are responsive to treatment with the attractants of the invention are *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella,* Agrotis spp., Euxoa spp., Feltia spp., *Earias insulana,* Heliothis spp., Helicoverpa spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Plodia interpunctella, Ephestia elutella,*Lacomobia spp., *Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana,* among others.

The method of the invention is limited to the insect species which attack fruit and nut trees, particularly immature, nonripe fruits, and those which are attracted to the attractant of the invention or to a blend containing the attractant of the invention and where a response is obtained of both male and female adult insect and/or larvae.

B. Formulations of the Invention

Attractants of the invention are formulated according to the intended use depending on whether the application is for a monitoring, disruption of mating, or attracticide ("attract and kill" or "lure and kill") strategy. Most preferred mode is to apply the formulation containing the attractant of the invention using lures, baits or traps placed in the orchards. However, the compositions according to the invention can be applied to the trees, plants or areas to be treated in the form of sprays, droplets, microfilms, microcapsules, or thin defined layers by using conventional devices known to those skilled in the art. For the latter purposes, the formulation may be formulated for controlled release. The formulation may be in the form of dispersion coating, film coating, spray coating, microencapsulated products, polymer slow release drops, globs, blocks, such as paraffin blocks, monoliths, puffers, and any such other similar form as known in the art. In each instance, the formulation may contain only the attractant of the invention, or the attractant and pheromone, or the attractant and insecticide or all three together.

Also suitable for the treatment of fruit-bearing trees is a process in which a defined amount of the formulations according to the invention is applied on the surface or to the stem of the plants with the aid of dosing dispensers, pipettes, spray nozzles or syringes, brushing devices, aerial sprays or surface nozzles to distribute the compositions over a substantially entire area. Also suitable is to incorporate the formulation according to the invention onto a solid carrier and/or a surface of any carrier or trap where it is allowed to harden, to cut up the resulting solid coatings or substrates and to attach the individual cut pieces at the sites where they are desired.

Various controlled-release systems suitable for the delivery of insect pheromones are described in *Controlled Delivery of Crop-Protection Agents,* Taylor and Francis, New York, (1990), Editor R. M. Wilkins, especially chapters 3 and 9 and in *Insect Suppression with Controlled Release Pheromone Systems,* Vol. I and II, CRC Press, Boca Raton, Fla. (1982). These control release systems include reservoir systems with rate-controlling membranes (micro- and macro-encapsulation), reservoir systems without rate-controlling membranes (hollow fibers and porous polymeric substrates and foams), monolithic (dissolved or dispersed) systems which can be non-erodible, erodible or degradable, and laminated structures. The publications cited are hereby incorporated by reference.

Monolithic systems, which may be used within the scope of the present invention, where the chemicals are incorporated (dissolved and/or dispersed) in polymeric materials include different types of rubbers and other elastomers and plastics such as poly(vinyl chloride), polyethylenes, polypropylenes, polyacrylates, poly(vinyl acetate), polyamides, polyesters, polycarbonates, polyurethanes and various combinations of the polymers. These monolithic materials can be used in both monitoring and "lure and kill" applications.

Formulations containing pesticides and attractants for "lure and kill" applications, which can be used within the scope of the present invention, include both the slow release flowable or viscous non-hardening matrixes described in U.S. Pat. No. 5,759,561 and the slow release compositions containing at least one curable polymer described in U.S. Pat. No. 5,707,638 which dry and harden to a sponge-like mass or a porous film. Both of these formulations are suitable for the distribution of the chemicals in the form of droplets or spots that adhere to a substrate such as foliage. The distribution of flowable, copolymeric pheromone-containing insecticidal compositions in the form of droplets that provide slow release of the pheromone is described in GP-PS 2,141,932. These patents and patent applications cited herein are hereby incorporated by reference.

range. They are generally on the order of magnitude which is conventionally chosen for the application of "attract-and-kill formulations" and/or mating disruption formulations.

C. Traps, Baits and Lures

Any type of traps, baits or lures, or trap-like stations, enclosures, platforms, etc., may be used for delivering the formulation of the invention comprising a volatile attractants from pear or apple extracts.

Examples of such traps which are used for illustrative purposes only and are not intended to be limiting may be found in U.S. patent applications Ser. Nos. 09/047,191 or 09/044,581, filed on Mar. 19, 1998.

The extract is typically incorporated into a monolith which may be of any polymeric matrix composition and colored red, white, gray, green, black or other suitable color.

It has been discovered that the best results in attracting the codling moth, males and female, are obtained with gray rubber septa.

TABLE 12

| Septa Insect | 0.1 mg A | | 1.0 mg A | | 3 mg A | | 10 mg A | |
|---|---|---|---|---|---|---|---|---|
| Population | ♂♂ ± SEM | ♀♀ ± SEM | ♂♂ ± SEM | ♀♀ ± SEM | ♂♂ ± SEM | ♀♀ ± SEM | ♂♂ ± SEM | ♀♀ ± SEM |
| Red Septa Low | 0.78 ± 0.55 | 0.43 ± 0.18 | 1.38 ± 0.60 | 1.06 ± 0.49 | 0.78 ± 0.35 | 0.69 ± 0.26 | 0.87 ± 0.41 | 0.57 ± 0.15 |
| Red Septa High | 1.04 ± 0.41 | 2.76 ± 0.80 | 2.21 0.72± | 4.12 ± 1.37 | 4.40 ± 1.28 | 6.46 ± 1.98 | 4.25 ± 0.99 | 7.04 ± 1.90 |
| Gray Septa Low | 0.97 ± 0.47 | 1.05 ± 0.49 | 1.13 ± 0.63 | 0.84 ± 0.30 | 2.02 ± 0.72 | 1.18 ± 0.37 | 1.29 ± 0.36 | 1.28 ± 0.33 |
| Gray Septa High | 5.88 ± 1.80 | 1.40 ± 0.52 | 3.86 ± 1.55 | 4.77 ± 1.34 | 6.20 ± 1.25 | 5.25 ± 1.33 | 3.59 ± 0.92 | 5.77 ± 1.30 |

| Septa Inset | 20 mg A | | 50 mg A | | Ph-L2 pheromone | | Solvent Bank | |
|---|---|---|---|---|---|---|---|---|
| Population | ♂♂ ± SEM | ♀♀ ± SEM | ♂♂ ± SEM | ♂♂ ± SEM | ♂♂ ± SEM | ♂♂ ± SEM | ♂♂ ± SEM | ♀♀ ± SEM |
| Red Septa Low | 0.94 ± 0.20 | 0.66 ± 0.15 | 0.57 ± 0.18 | 0.74 ± 0.24 | 0.80 ± 0.31 | 0 | 0 | 0 |
| Red Septa High | 2.87 ± 0.88 | 5.43 ± 1.78 | 3.63 ± 0.93 | 7.30 ± 2.00 | 9.98 ± 2.94 | 0.06 ± 0.06 | 0 | 0 |
| Gray Septa Low | 2.97 ± 0.97 | 2.83 ± 1.07 | 2.04 ± 0.83 | 1.79 ± 0.69 | 1.28 ± 0.61 | 0 | 0 | 0.04 ± 0.03 |
| Gray Septa High | 6.14 ± 1.46 | 3.59 ± 1.46 | 6.18 ± 1.60 | 10.15 ± 2.04 | 0.05 ± 0.05 | 0.08 ± 0.05 | 0.11 ± 0.07 | |

Low = tested in a low population organic orchard.
High = tested in a high population conventional orchard.

Other slow release formulations suitable for disruption strategies include utilizing the attractants, with or without pheromone, in a micro- or macro-encapsulated form. For this purpose, the attractants of this invention are encapsulated in a suitable polymer or mixed polymers of synthetic or natural origin and can be released through the walls of the micro- or macro-capsules slowly or in a controlled manner. The compounds can also be incorporated into a granulate matter that is capable of releasing them slowly and in a controlled manner. The granulate matter can consist of small-particled inorganic carriers and/or organic polymers such as those familiar to a person skilled in the art. Other formulations suitable for disruption strategies include hollow fibers, laminated structures, ropes of various materials and puffers which release chemical at timed intervals.

The amounts in which the compositions according to the invention are applied can be varied within a substantial Since there have been differences observed between traps containing gray, white or red septa, a study was performed to determine the significance of the specific septa and their effect on the increase or decrease of attractancy. The gray rubber septa, in particular, was found to enhance the attraction. Results are seen in Table 12.

As seen from Table 12, gray septa delivered substantially more attractant than red septa, which were specially pre-treated but nevertheless still had lower delivery rate.

D. Laboratory and Field Testing

One aim of this invention was to discover and develop the use of these volatile attractants in attracticide (lure and kill) formulations of attractant and insecticide targeted at killing the neonate, newly hatched, larval worms. These attracticide formulations would be sprayed or splattered on leaves (the site where eggs are normally laid) and would attract and kill (by contact or ingestion) the newly-hatched neonate larvae before the larvae crawl and find a fruit or nut to bore into and damage.

As described above, to achieve the effective control of larvae and adult moths and other fruit pests, the pear and apple volatiles were isolated and purified and new blends were developed comprising of the attractants of the invention alone or in combination with sex pheromone of the insect to be trapped and annihilated or mating disrupted, or in combination with insecticide to kill the insect, or in combination with both the sex pheromone and insecticide and optionally with other additives.

In the studies performed during development of the invention, headspace odor emissions were collected and chemically identified by GC-MS of both host pome fruit trees and host-walnut trees. The candidate compounds were then selected for bioassaying by comparing common vs. novel volatile constituents of the fruit and nut odors. The chemical analyses were followed by field testing of blends of synthetic chemically-related volatiles and individual volatiles for their ability to directly evoke behaviors or augment/improve the attractancy of commercially-available pheromone monitoring traps.

Details of the chemical identification and behavioral bioassays are described in Examples 1 and 2. Purification and synthetic methods used for preparation of synthetically prepared, substantially pure compounds are described in Example 3.

1. Comparative Odor Profiles of English Walnuts, Apples and Pears

The odor profile of English walnuts (whole nuts with intact green husks) was found to be mainly terpenoid in composition, having a balance of monoterpenoids and sesquiterpenoids. A number of terpenoid peaks observed in walnuts are shared by the pome fruits and walnuts, but many more compounds were found solely in the pome fruit odors. The pome fruit odor profiles were distinct due to a large number of aliphatic esters and alcohols present in these pome fruit odors.

2. Inherent Attractancy Screening of HPV Blends

Twenty-five HPV blends and eight individual compounds were field tested. One synthetic blend, "ester blend #10," elicited excellent codling moth attraction. In field tests, the other tested blends (see Table 3) and compounds captured no moths over a three month period, except for an "apple-skin surface extract" (Golden Delicious, ether solvent) (Σ=3 codling moth captured, 1♂: 2♀♀) and the individual compound, (E,E)-α-farnesene (Σ=1♂ codling moth captured). The field tests are presented in Table 3 and show attraction specificity for HPV ester blend #10.

Attraction of female and male codling moths to ester blend #10 in baited sticky trap is seen in FIG. 1. As seen in FIG. 1, HPV ester blend #10 acted as a bisexual-lure, attracting both sexes of codling moth but differentially attracting/capturing twice as many females than males in sticky wing-traps in the early flight. Results are numerically expressed in Table 13.

TABLE 13

| Moths/Trap/Night: | Male Capture: | Female Capture: |
|---|---|---|
| Female Dominated Attraction Ester Blend #10-Baited Sticky Trap | | |
| Mean ± SEM | 0.70 ± 0.23 | 1.50 ± 0.36 |
| Sum: | 30.0 | 64.7 |
| T-test, p= | 0.002 | |

TABLE 13-continued

| Moths/Trap/Night: | Male Capture: | Female Capture: |
|---|---|---|
| Male Attraction Pheromone-Baited Sticky Trap | | |
| Mean ± SEM | 4.96 ± 1.04 | 0 |
| Sum: | 94.3 | 0 |

Table 13 compares two orchard treatments with ester blend #10 and pheromone-only baited sticky traps. As seen from Table 13, in the traps baited with ester blend #10, more than twice the number of females were captured than males. In the pheromone baited traps, only male insects were captured.

These results on codling moth attraction were found at both the low- and moderate-population density Hartley variant orchards, both conventional and organic.

The female flight pattern depicted by capture in ester blend #10-baited sticky traps was related to the male flight pattern to pheromone-baited traps over the 3 month test period. Results are seen in FIG. 2, which is a comparative graph of codling moth flight patterns delineated by males captured in pheromone traps versus both sexes captured in ester blend #10 traps. The female flight pattern defined by ester blend #10 varied from that of the male pattern defined by the pheromone, not by the general curve shape, but by capturing fewer codling moths at most trap checks (approx. 44% of pheromone capture) as seen in Table 11 and by a temporal-phase shift of the curves for each emergence/flight as seen in FIG. 2. The male pheromone curve rises sooner and lasts longer per flight, while the female ester blend #10 curve drops off sooner. These temporal-phase shifts of the flight curves represent the earlier and longer emergence of male codling moth for each flight period.

A question of gender specificity of response, that is, are male codling moths really attracted to ester blend #10 or are they just following or being lured-by the initially-attracted females, was also investigated.

Because females can remain alive even in the summer heat on sticky trap liners for a couple of days, they conceivably emit pheromone, thus causing attraction of males.

Experimental challenge to this question was to use a novel, funnel-liquid-jar-trap ("rapid-kill liquid traps") to rapidly kill (drown) attracted moths. The results shown in Table 14 of one month of replicated trapping (3 traps and 12 trap-check dates) with these rapid-kill liquid traps demonstrated that ester blend #10 is truly a bisexual codling moth lure. Again, it was the females who were predominantly captured (sex ratio: 1♂:3.0♀♀ insect attracted).

TABLE 14

| Moths/Trap/Night: | Male Capture: | Female Capture: |
|---|---|---|
| Ester Blend #10 | | |
| Mean ± SEM | 1.03 ± 0.23 | 3.07 ± 0.57 |
| Sum: | 31.8 | 95.3 |
| T-test, p= | <0.001 | |
| Pheromone | | |
| Mean ± SEM | 3.04 ± 0.08 | 0 |
| Sum: | 18.3 | 0 |

Table 14 shows (upper part) female dominated attraction of codling moths to ester blend #10 baited rapid kill liquid traps and male attraction (lower part) to a pheromone only baited rapid-kill liquid traps. Again, females were preferentially attracted (3:1 ratio) to ester blend #10 rapid kill liquid traps, while only males were seen to be attracted to the pheromone traps.

Figure 4:
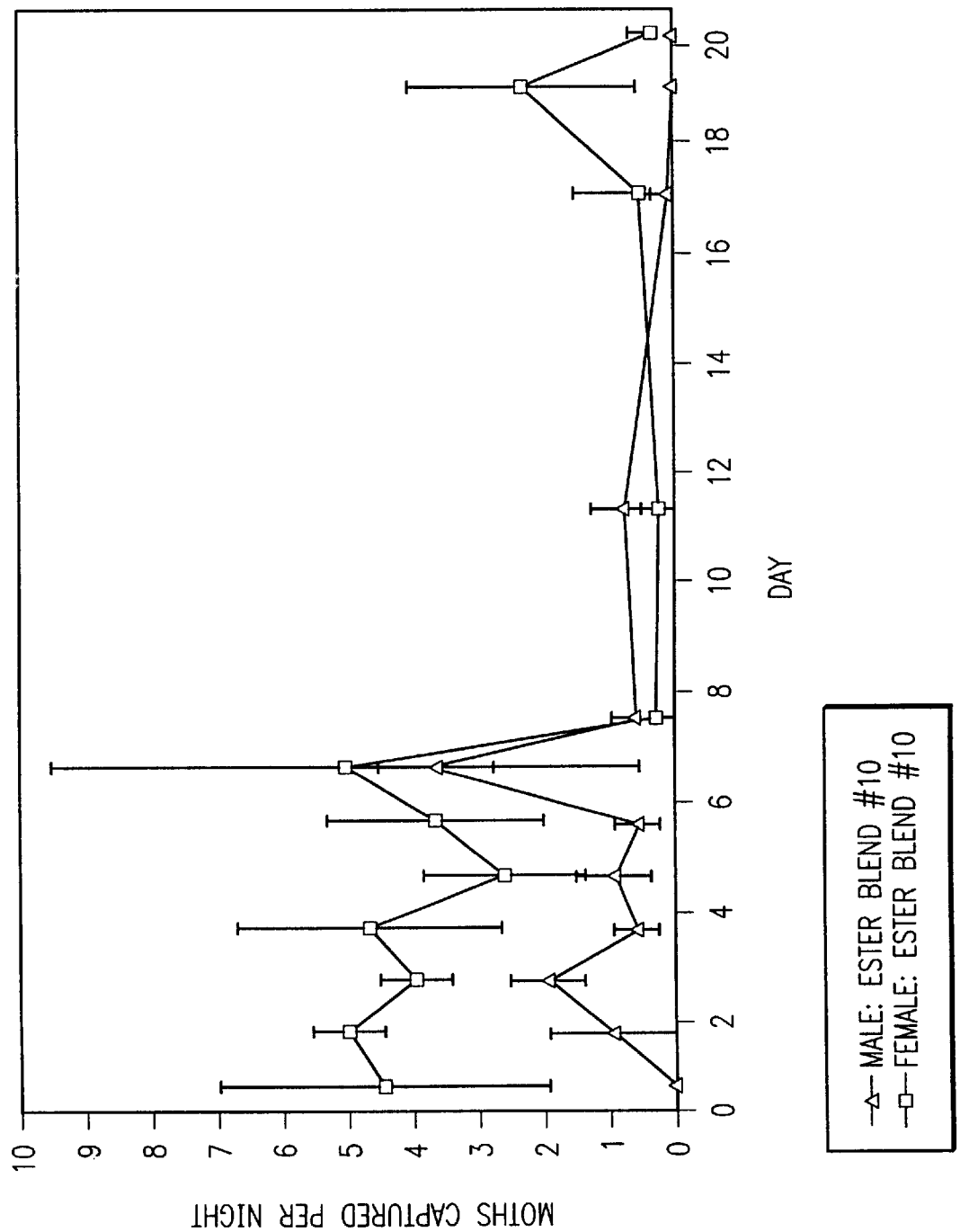
FIG. 4 is a graph representing mean attraction of female and male codling moths to rapid-kill traps baited with a pear extract blend (ester blend #10). Male codling moth (-Δ-), female codling moth (-□-).

FIG. 4 shows mean attraction of female and male codling moth to ester blend #10 baited rapid-kill liquid traps.

With these rapid-kill liquid traps, the ester blend #10-baited traps caught 69% of the number of codling moth caught in this type of trap baited with pheromone over the same interval.

A question of compound specificity, that is, are codling moths attracted solely by the four-component ester blend #10 or by the individual pear volatile components of this blend or various binary combinations of blend components, was also investigated.

In a 2½ month replicated experiment (3 traps reps and 43 trap-check dates) using sticky traps, it was found that one compound present in the ester blend #10, namely ethyl (2E,4Z)-2,4-decadienoate accounted for most of the attractancy and specificity activity of the blend as seen in Table 15.

TABLE 15

| Moths/Trap/Night: | Male Capture: | Female Capture: |
|---|---|---|
| Ethyl (2E, 4Z) - 2,4-decadienoate | | |
| Mean ± SEM | 0.58 ± 0.12 | 1.78 ± 0.45 |
| Sum: | 24.9 | 76.4 |
| T-test, p= | 0.005 | |
| Pheromone | | |
| Mean ± SEM | 4.96 ± 1.04 | 0 |
| Sum: | 94.3 | 0 |

Table 15 shows female dominated (upper part) attraction of codling moth to single compound ethyl (2E,4Z)-2,4-decadienoate baited sticky trap, using 3 traps and 43 trap checks, and male attraction (lower part) of codling moths to a pheromone-only baited sticky trap (1 trap, 19 trap checks).

Ethyl (2E,4Z)-2,4-decadienoate attracted codling moths at the same rate and numbers as the ester blend #10 and continued to attract primarily females (sex ratio: 1♂:3.1♀♀). Results are seen in FIG. 5.

Figure 5:
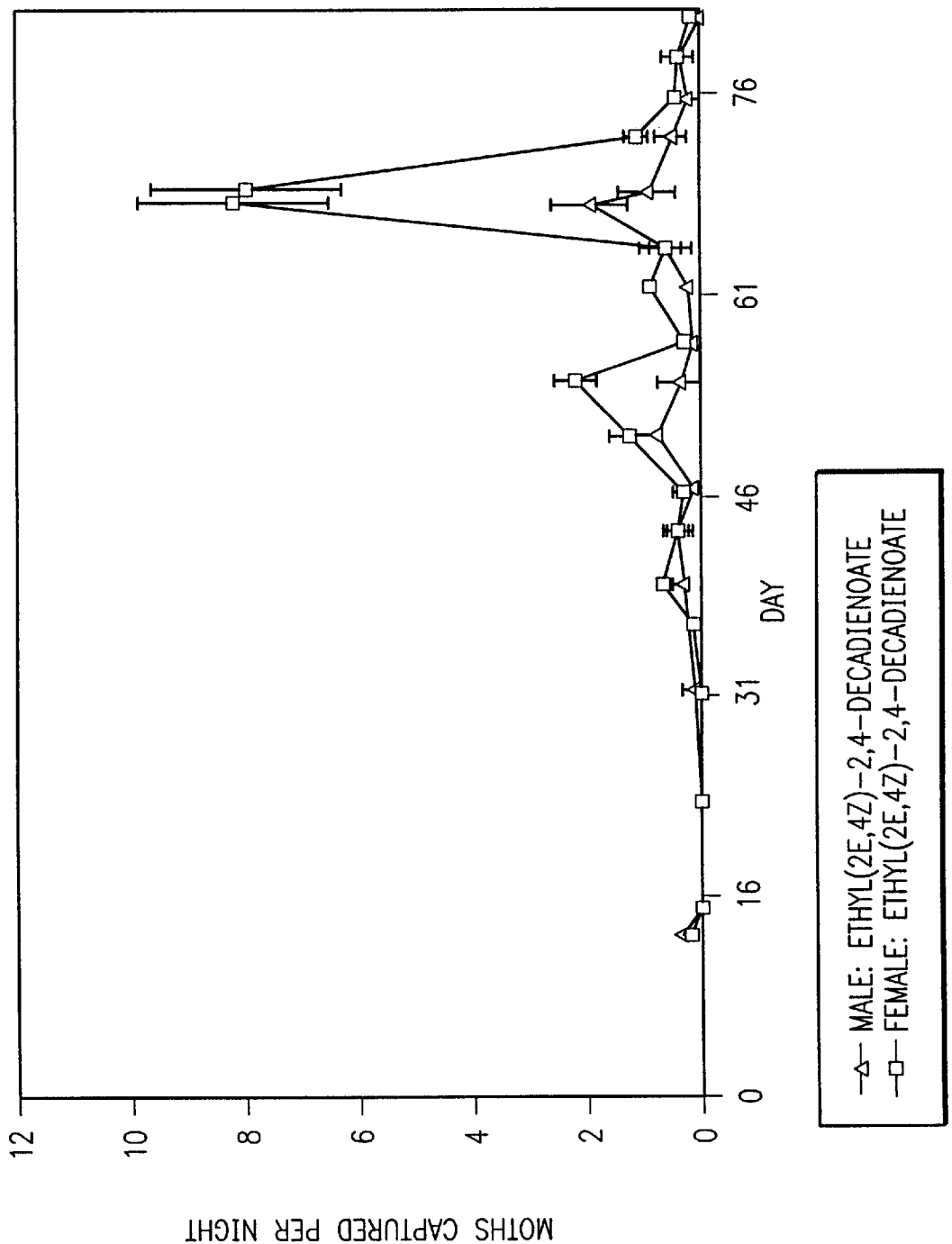
FIG. 5 is a graph representing mean attraction of female and male codling moths to sticky traps baited with a single pear extract compound, ethyl (2E,4Z)-2,4-decadienoate. Male codling moth (-Δ-), female codling moth (-□-).

FIG. 5 illustrates mean attraction of female and male codling moths to sticky traps baited with a single host plant volatile, ethyl (2E,4Z)-2,4-decadienoate. The attraction was followed over a two month period. As seen in FIG. 5, this compound was approximately 48% as attractive as pheromone (Table 15), and generated a flight pattern similar to that of males to pheromone with the temporal-phase shift of the flight curves described above.

Additionally, the question of whether codling moths are attracted to ester blend #10 in apple and pear orchards or just in walnut orchards, orchard context selectivity was studied.

An experiment was conducted using sticky traps-baited with ester blend #10 and hung in apple, pear and walnut cultivars located in separate varietal plots for the three host-trees at the horticultural orchards. Traps were checked 24 times over a six month period.

In the mixed-variety apple plot, 60% of the codling moths captured were females (mean of 2.36 moths for females and 1.45 for males) in ester blend #10-baited traps and the total capture was 24% of that of males captured in pheromone-baited traps. Similar results were found in tests in pear orchards.

Figure 6:
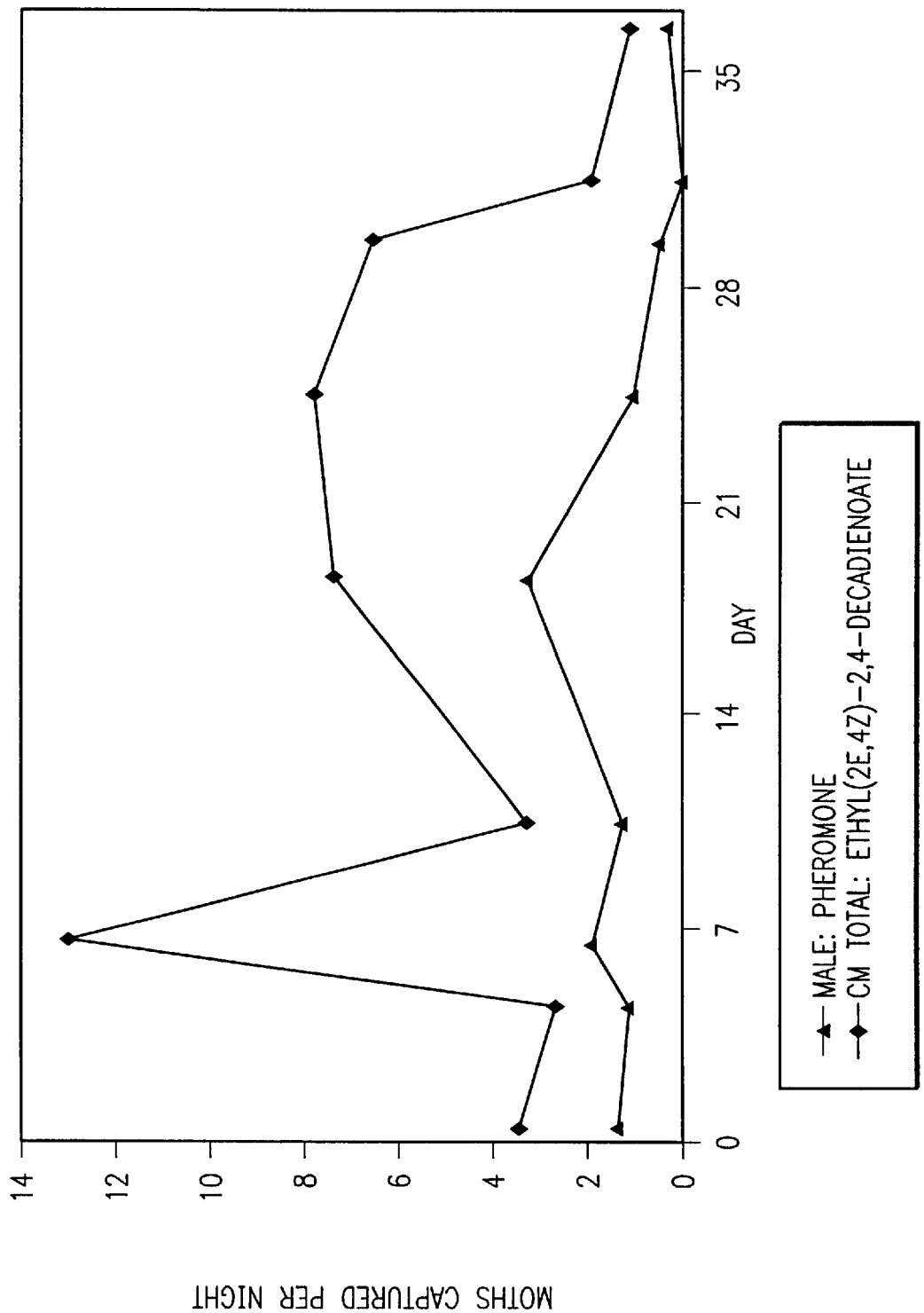
FIG. 6 illustrates the capture of male and female codling moths in pheromone vs. ethyl (2E,4Z)-2,4-decadienoate-baited traps in a pheromone permeated mating disruption walnut orchard. The ability to detect males and females is illustrated in a mating disruption orchard.

FIG. 6 illustrates total capture of codling moth males and females, in a mating disruption treated orchard by using pheromone lures (-▲-) and by using lures containing ethyl (2E,4Z)-2,4-decadienoate (-♦-) (10 mg/lure)

As seen from FIG. 6, the ester attractant was very potent and captured more than double the number of codling moths than the lures with pheromone only. This demonstrates that the attractant is an effective population monitoring tool in orchards using pheromone mating disruption applications.

Figure 7:
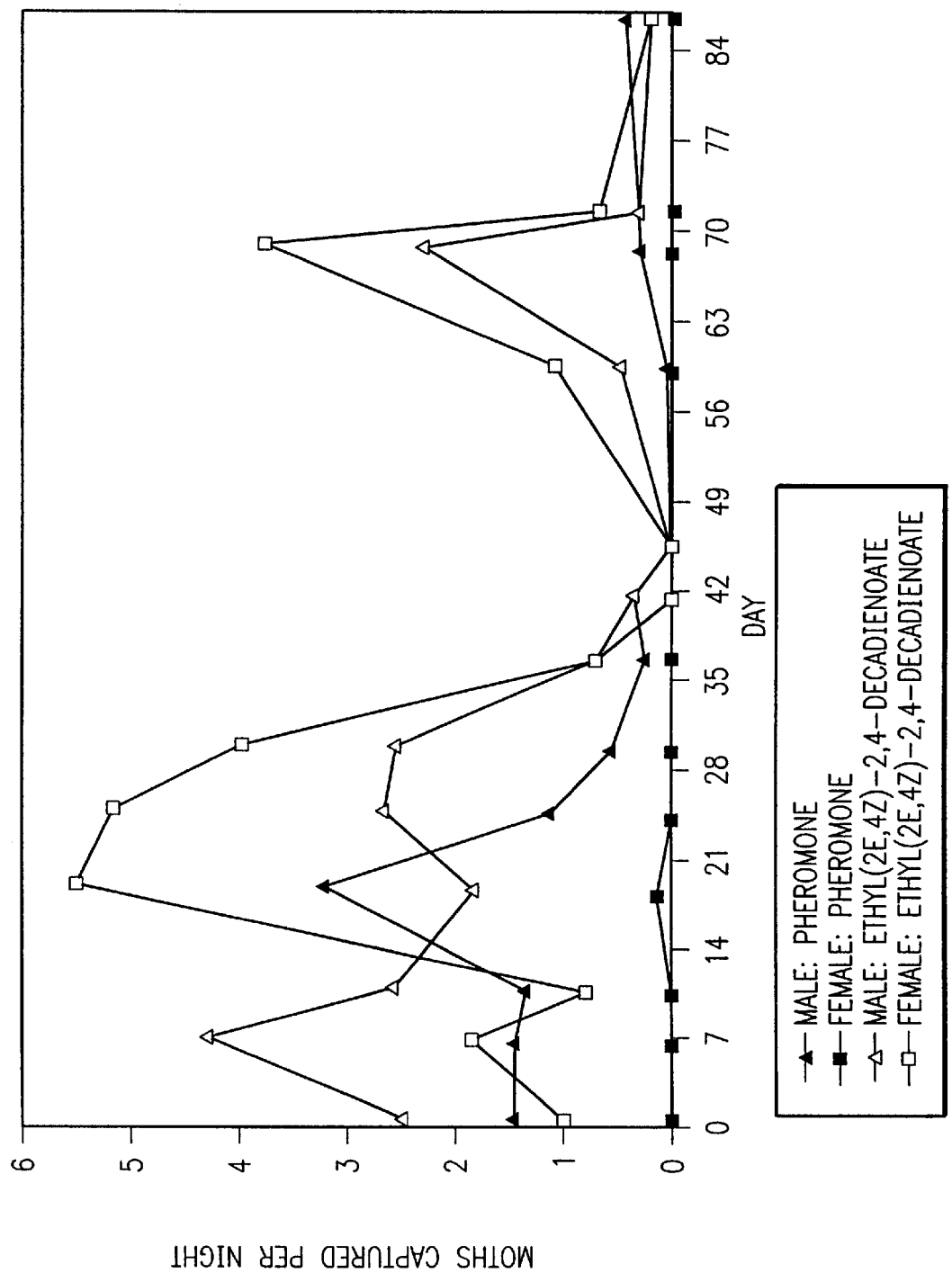
FIG. 7 shows detection of males and females of the codling moth separately, lured with a sex pheromone or with ethyl (2E,4Z)-2,4-decadienoate. Male capture with sex pheromone (-▲-), female capture with sex pheromone (-■-), ale capture with ethyl (2E,4Z)-2,4-decadienoate (-Δ-) and female capture with ethyl (2E,4Z)-2,4-decadienoate (-□-).

FIG. 7 shows capture of males (-▲-) or females (-■-) into traps containing pheromone lures only and into traps containing ethyl (2E,4Z)-2,4-decadienoate, males (-Δ-) females (-□-) in a mating disruption treated walnut orchard.

As seen in FIG. 7, there were no females captured in traps with pheromone only. As expected, a large number of males was captured with the pheromone lure. As to the ester lure, a larger number of males was captured in ester lure traps than those containing only pheromone. Of the moths captured in ester lure containing traps, the greater number were females.

These findings clearly support the discovery of novel female attractants derived from pear or apple extracts.

In one mixed variety apple orchard, although ethyl (2E,4Z)-2,4-decadienoate attracted both males and females, more males than females were captured (see FIG. 8) in the test.

Figure 8:
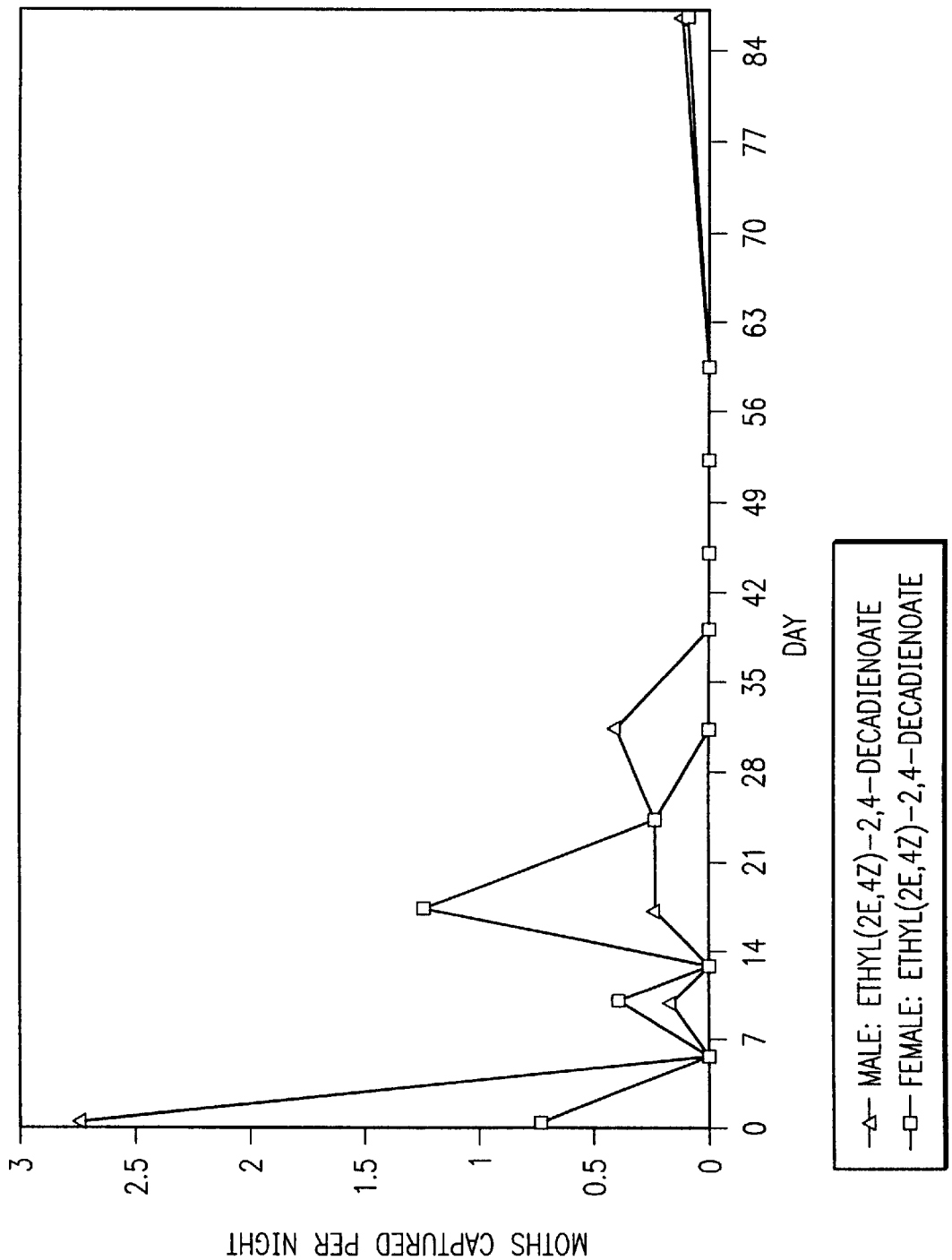
FIG. 8 illustrates male (-Δ-) vs. female (-□-) codling moth capture per night with the ethyl(2E,4Z)-2,4-decadienoate lure in an apple orchard.
Figure 9:
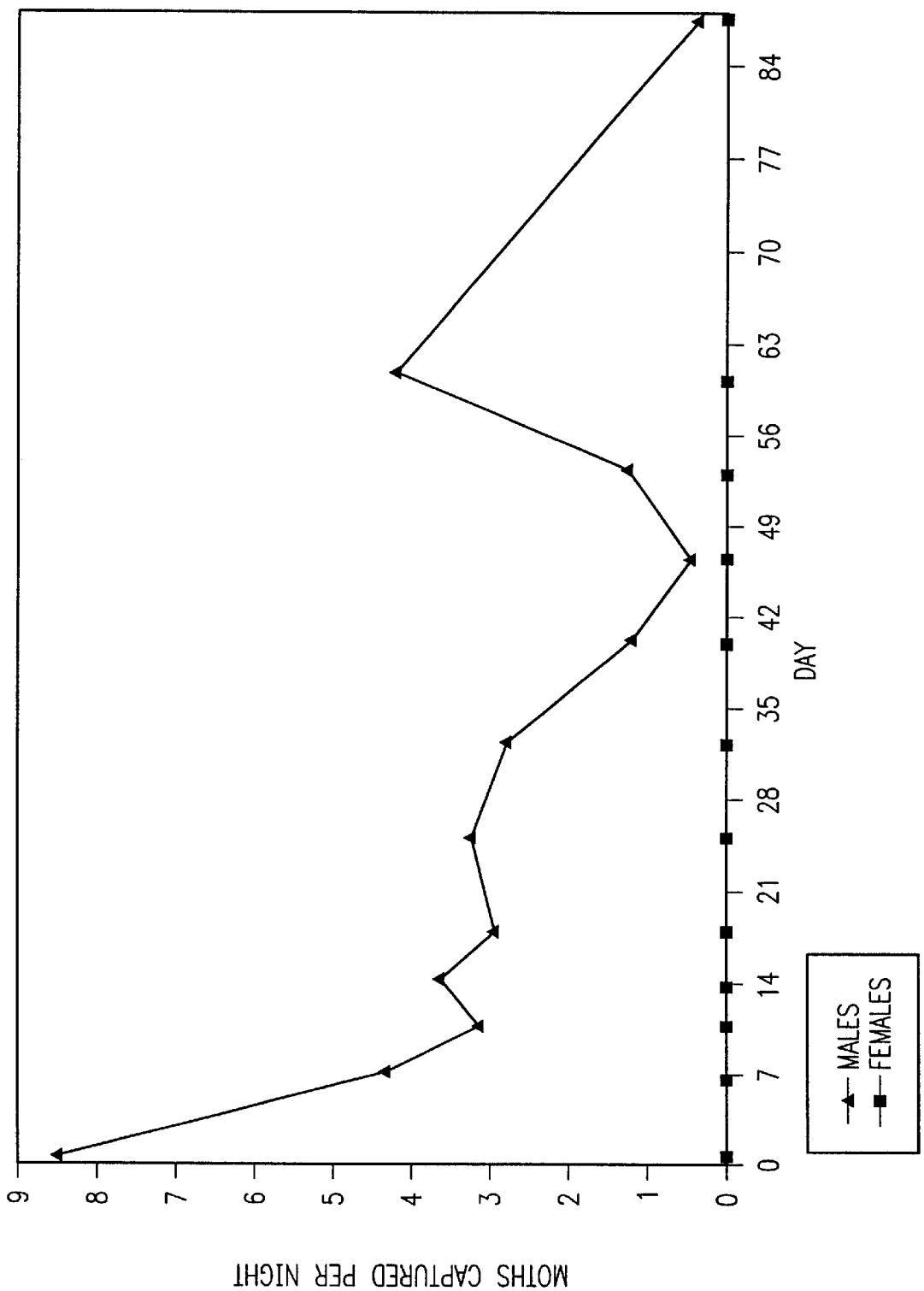
FIG. 9 illustrates male (-▲-) vs. female (-■-) codling moth capture per night with the codling moth sex pheromone in an apple orchard.

FIG. 9 shows the same study as in FIG. 8, except that the trap contained pheromone rather than the ester attractant.

As seen in FIG. 9, a large number of male codling moths was captured with sex pheromone (-▲-).

Figure 10:
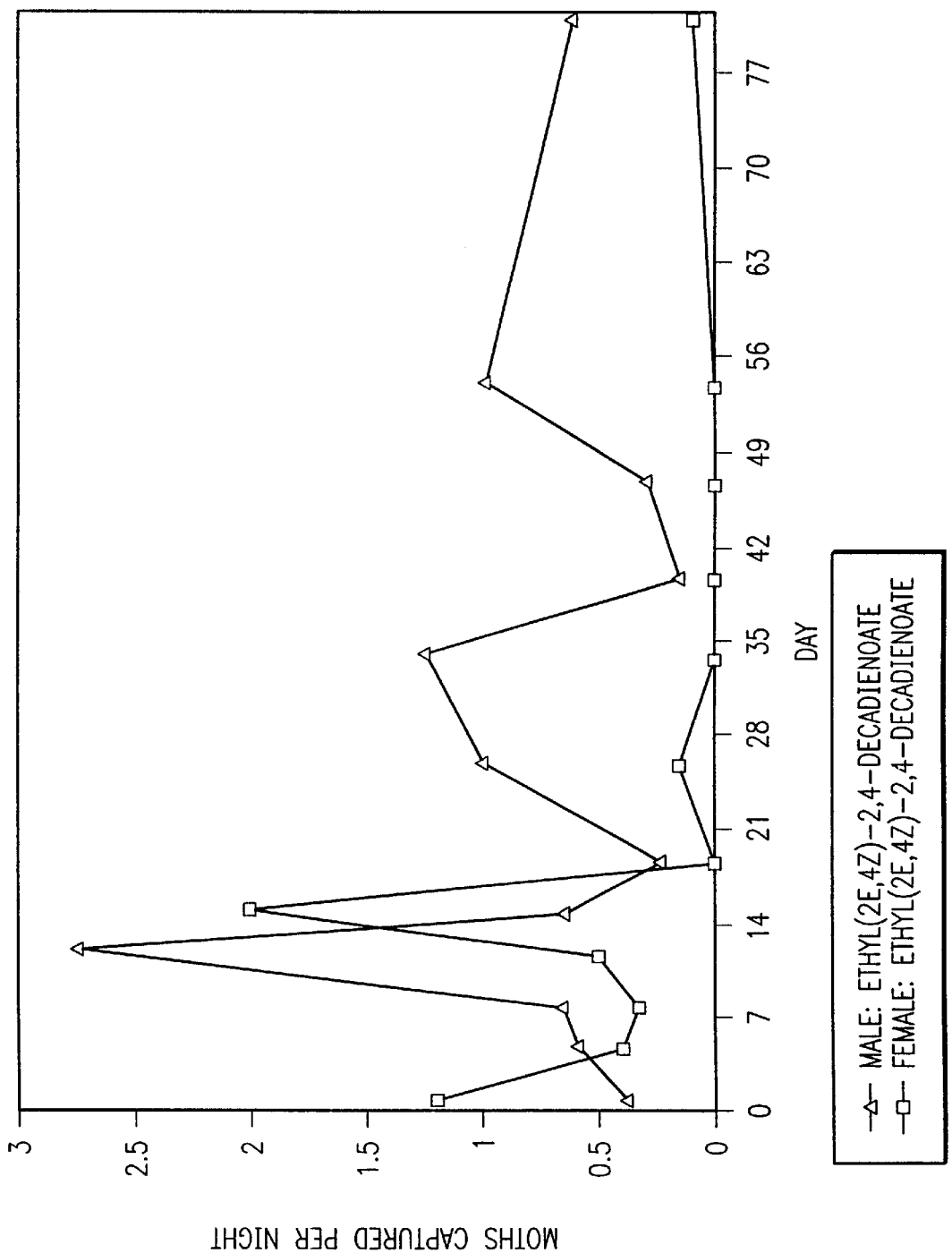
FIG. 10 illustrates male (-Δ-) vs. female (-□-) codling moth capture per night with the ethyl (2E,4Z)-2,4-decadienoate lure in a pear orchard.

In one pear orchard, when codling moth capture in traps containing ethyl (2E,4Z)-2,4-decadienoate was followed, both the number of males (-Δ-) and females (-□-) captured was highest at the beginning of the field testing but leveled off, particularly for females, in the later stage of the test, as seen in FIG. 10.

Figure 11:
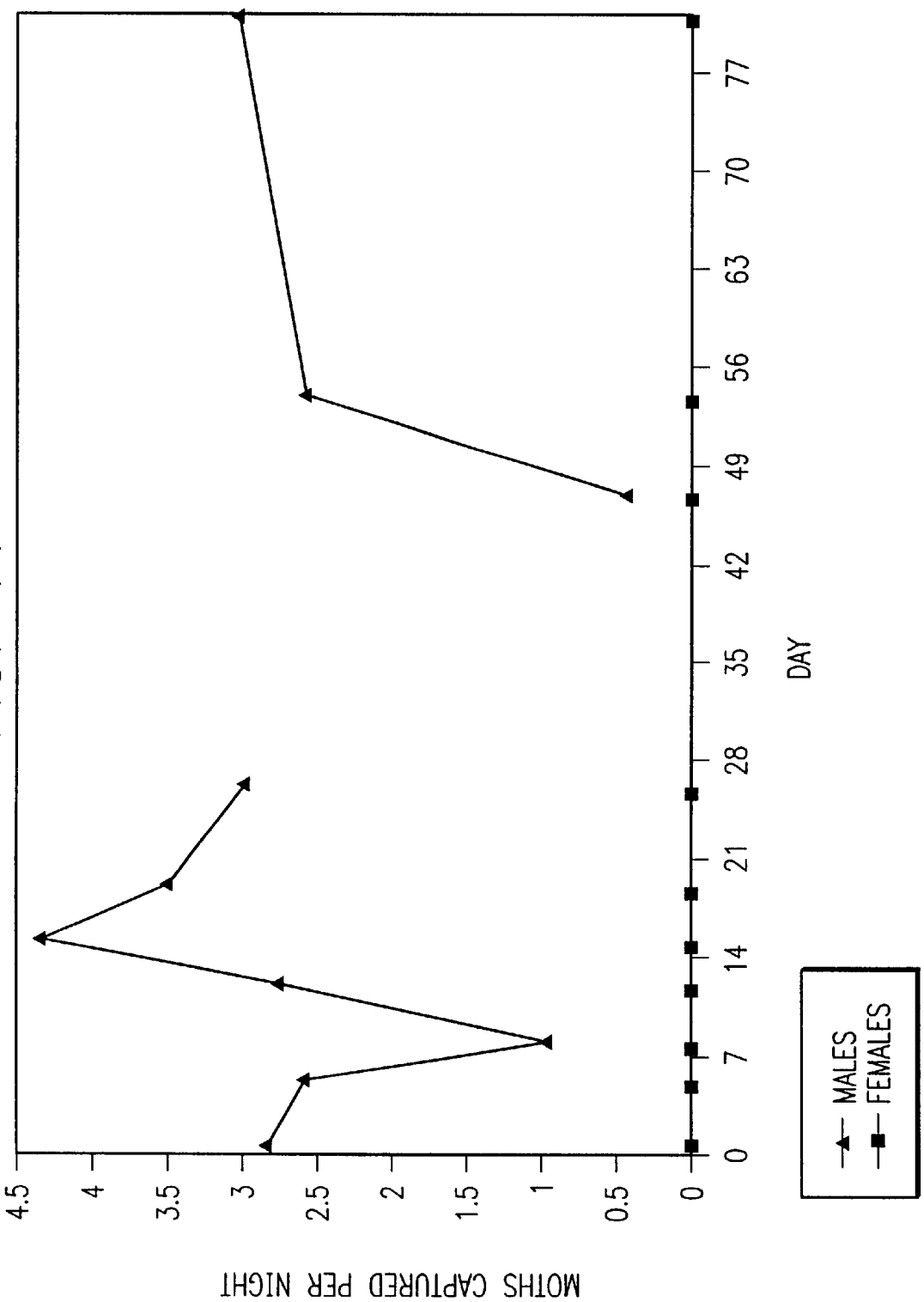
FIG. 11 illustrates capture of male (-▲-) vs. female (-■-) codling moth per night with the codling moth sex pheromone in a pear orchard. The break in the curves indicates the loss and replacement of septa containing the pheromone.

In the same pear orchard study in traps with pheromone only, as seen in FIG. 11, there were no females (-■-) captured and a large number of males (-▲-) was captured, as expected. The gap in the cure in the FIG. 11 in this test was caused by the temporary loss of the pheromone septa from the trap followed by its replacement.

Figure 12:
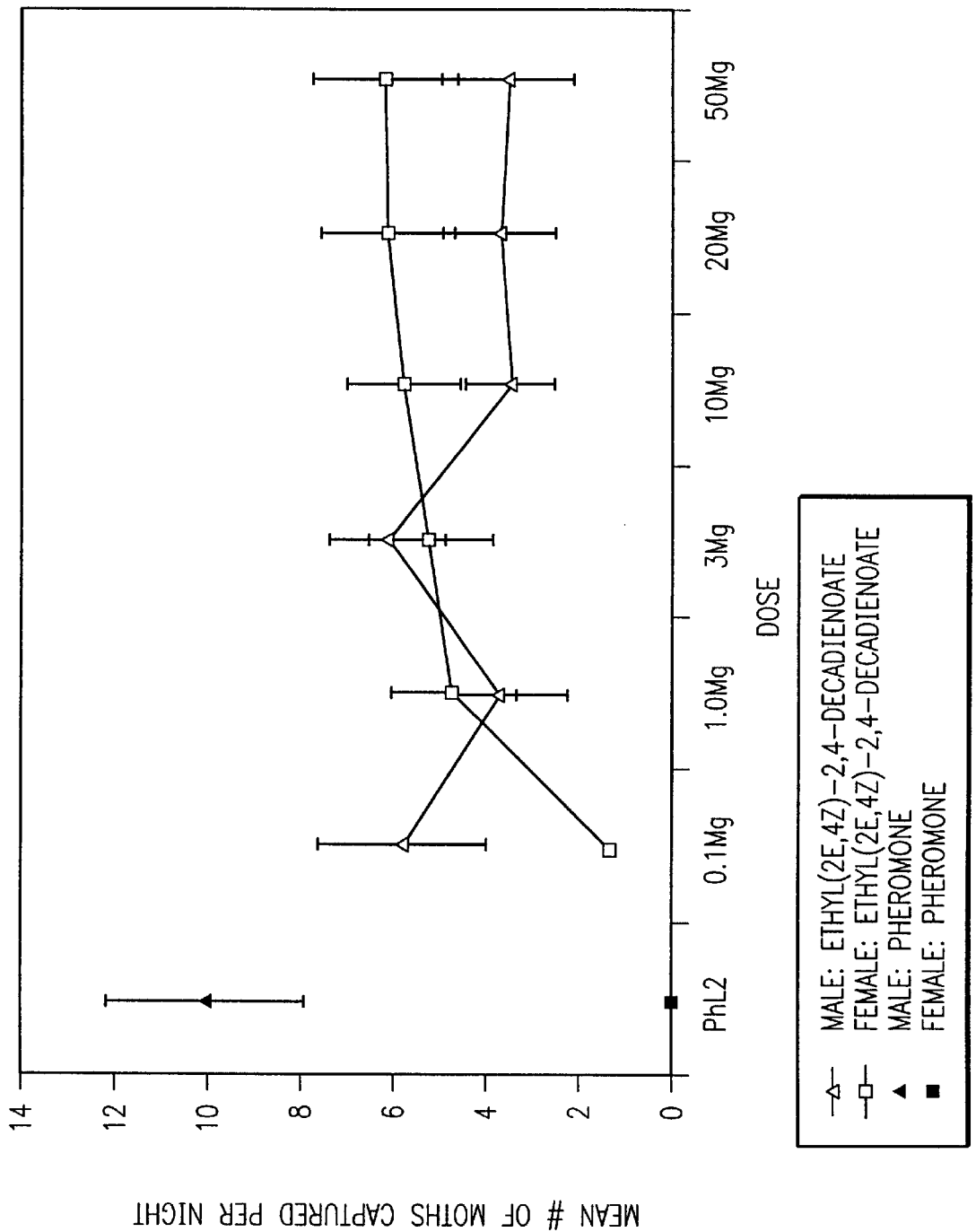
FIG. 12 illustrates capture of the codling moth males (-Δ-) vs. females (-□-) with ethyl (2E,4Z)-2,4-decadienoate in the dose concentration range from 0.1–50 mg in grey septa vs. males captured with pheromone at a fixed dose of 3 mg.

FIG. 12 depicts the mean number of captured codling moths plotted versus the loading dose concentration from 0.1-50 mg of the ester attractant. FIG. 12 clearly shows that more females (-□-) than males (-Δ-) were captured during this study and that the number of captured females clearly depended on the ester concentration.

Figure 13:
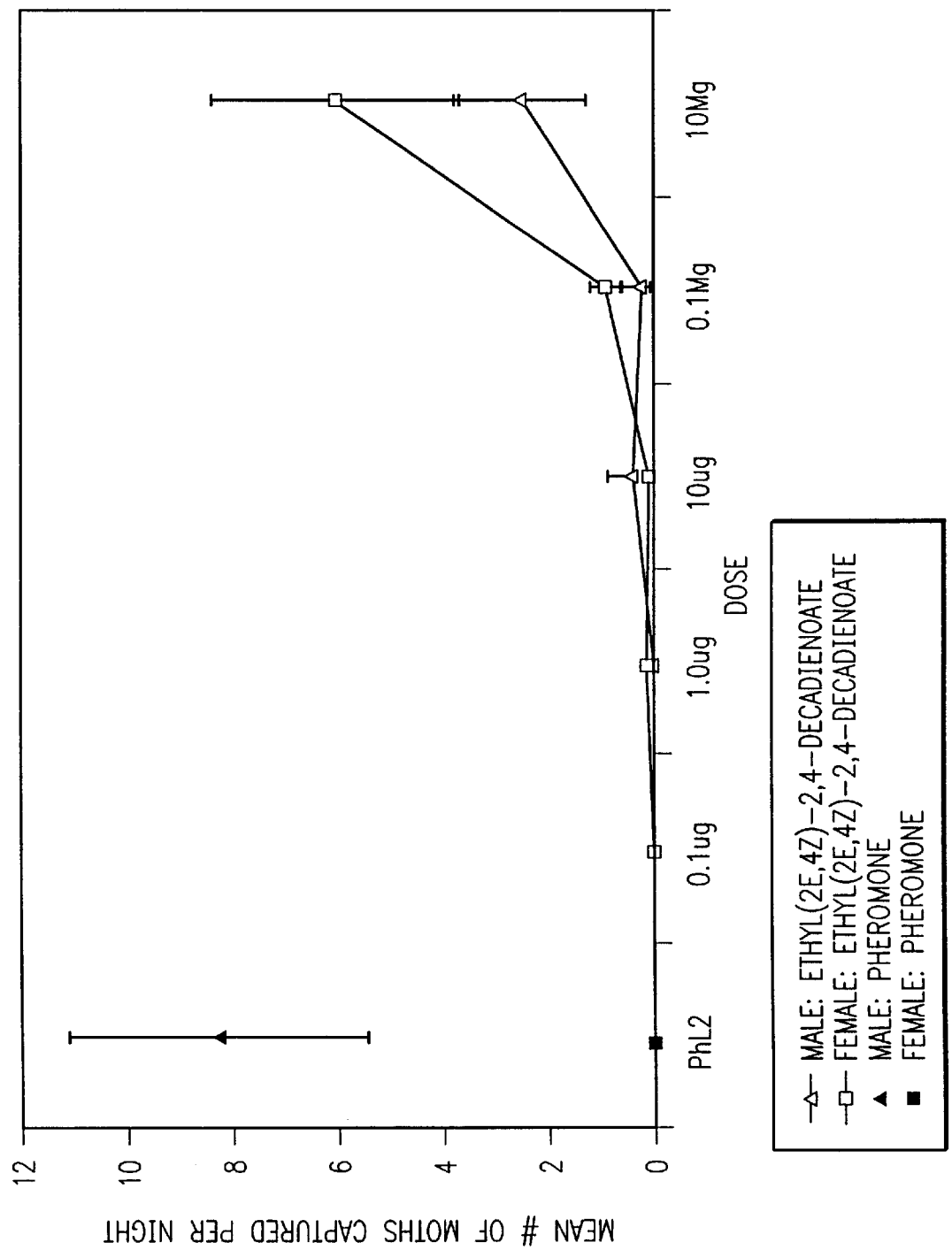
FIG. 13 illustrates capture of the codling moth males (-Δ-) vs. females (-□-) with ethyl (2E,4Z)-2,4-decadienoate in the lower dose concentration range from 0.1 μg-10 mg in grey septa vs. males captured with pheromone at a fixed dose of 3 mg.

FIG. 13 shows a similar study except that the loading dose concentrations of the ester attractant were lower, (from 0.1 μg to 10 mg). In this study, both males (-Δ-) and females (-□-) responded to a threshold dose of less than 10 μg of the ester attractant, while at progressively higher loading rates females were more responsive than males.

3. Attractancy to Larvae

In order to confirm that the attractants of the invention, are able to achieve almost complete control of insect pest infestation, their effect on larval orientation was further investigated. Results shown below in Table 16 show that the attractants of the invention do indeed attract the larvae to its source, and also that they cause the larvae to arrest and aggregate in one place close to the attractant source.

Behavioral orientation responses in the laboratory of first-instar or neonate larval worms of the codling moth are seen in Table 16. Data shown in Table 16 represents means of to 50 bioassay replications using five neonates per experiment conducted in small areas (10 cm diameter petri dishes). Experiments were dual-choice tests, where the released neonate larvae crawled and made perceptual choices between two small (one cm diameter) filter paper discs, with one disk treated with 1 ug or 10 ug of ethyl (2E,4Z) decadienoate and the other disc treated with an equivalent volume of solvent (methylene chloride).

TABLE 16

| Disc Treatment: | Attraction; average number of neonates contacting disc: x ± SEM | Latency: average time (sec) to first arrive at disc: x ± SEM | Arrestment; average time (sec) on or under disc: | |
|---|---|---|---|---|
| | | | 1 ug dose of attractant a | 10 ug dose of attractant |
| Ethyl (2E, 4Z) Decadienoate | 4.5 ± 0.9 | 74.5 ± 16.1 | 19.7 ± 5.6 | 33.0 ± 10.7 |
| Solvent Control | 0.5 ± 0.5 | 123.7 ± 34.2 | 11.4 ± 3.4 | 10.0 ± 2.5 |

Statistical tests on the larval orientation data show that for all three parameters the response of neonate codling moths to ethyl (2E,4Z)-decadienoate significantly exceeded the response to the solvent control. Thus, ethyl (2E,4Z)-decadienoate acts as a superior larval attractant and arrestant for the codling moth and would show practical use as the attractant in attracticide lure and kill formulations applied to the foilage and fruit of trees. The bioassay area used was about 10 cm in diameter while an average leaf ranges from nine to 15 cm in length and a neonate must crawl on average more than 20 cm from the leaf oviposition site to the nearest fruit to infest, thus allowing adequate opportunity to sense and encounter an attracticide droplet.

Utility

The novel host plant volatile attractants of the invention are useful in attracting and luring both sexes of insect pests of lepidopterous species and, therefore, provide new, specific, effective and precise semiochemical monitoring and/or killing and overall control for insect pests of lepidopterous species, as follows:

1) monitoring female and male populations and emergence/flight patterns thereby allowing for increased effective timing of insecticides use to coincide with the period when the newly hatched larvae are also present;
2) critical monitoring of pest emergence patterns in mating disruption orchards where monitoring with pheromone traps is difficult or impossible;
3) controlling and disrupting mating;
4) crucial "in-season" assessment of mating disruption efficacy by attracting/collecting females, and assessing whether they have been prevented from mating;
5) use as the "bisexual adult attractant" in direct control strategies attracting, luring, mass-trapping or attracticide of male and female insect pests;
6) use as an adult attractant, aggregant, and arrestant, as ovipositional or feeding stimulant or in attracticide direct control methods; and
7) use as a larval/worm stage attractant, aggregant and arrestant, or feeding stimulant or in attracticide direct control methods.

Key attributes of HPV-based larval and bisexual adult attractants are their novelty, that is, discovery of new, unique host plant-derived bisexual moth attractants for both larvae and adults; their specificity, that is, they attract only lepidopterous species, especially codling moths; uniqueness, that is, they attract both sexes, particularly females; potency, that is, they have approximately 50% to equal or better potency of the pheromone; context selectivity, that is, unique pear volatile are effective in walnut and pome fruit orchards; practicality, that is, the attractants can lure virgin or fertile females and delineate female flight-patterns; and enhancement properties, that is, they are effective in presence of pheromone and such effectivity is enhanced by the presence of pheromone.

A novel application of the HPV-based dual larval and adult bisexual lures are various "attracticide" or "lure and kill" strategies targeted uniquely at both adult moths and egg-laying females and larval neonate worms. The lure can be used with either conventional insecticides or with transformed "BT-trap-tree" cultivars. Additionally, a lure for a gravid-female is the crucial requisite for application of the ovipositional "trap-trees" used in the attracticide control strategy.

Another novel application of these HPV-based bisexual lures are their use in combination with species specific pheromones to increase the effectiveness and specificity of disrupting the orientation, attraction, flight and mating of males in mating disruption strategies.

EXAMPLE 1

Extraction and Analysis of Volatile Semiochemical Attractants

This example describes extraction, isolation and analysis procedures used to obtain individual volatile odors of various apple, pear or walnut varieties.

Both solvent extraction and headspace odor trapping were used for odor isolation and analysis of the complex odors of various apple varieties, Bartlett pears and English walnut varieties.

Stainless steel tubes packed with Tenax® adsorbent were used with a battery-powered small vacuum sampler pump to trap the volatile leaf and fruit odor emissions of various host-plant trees in the laboratory and orchard. The odor tubes were either extracted by solvent washes or thermally-desorbed onto a DB-1 capillary GC-MS system and compositionally analyzed. Differential compositional analysis identified almost 100 volatile compounds found in pome fruit odor but not in walnut odor.

Synthetic samples of 92 chemically-diverse pome fruit HPVs were variously mixed to create 23 distinct recipe blends, that were formulated based on a blend's components sharing a common carbon-chain length and/or functional group moiety (e.g., monoterpenes, sesquiterpenese, alcohols, aldehydes acetate esters, etc.). These 23 distinct blends were then tested to judge if they were attractive to codling moth.

EXAMPLE 2

Behavioral Bioassays

This example describes behavioral bioassays used to determine the effect of host-plant volatiles on the insect pest.

To determine the effects of HPVs on both primary attraction and pheromone attraction of codling moths, two experiments were conducted: 1) tests of the inherent attractancy of the HPVs to both sexes of the codling moth, and 2) the preference of male codling moth for either pheromone alone or pheromone augmented with HPVs.

Inherent Attractancy Tests

Sticky traps (ICP and IIB traps, Trécé, Inc. Salinas, Calif.) were baited with either extracts, blends of HPVs, or individual HPVs (>95% purity) that evaporated from impregnated rubber septa. HPV blends, or individual HPV compounds, were diluted in hexane and pipetted onto rubber septa at approximate doses of 10 mg/septum. A single treatment septum was placed in each sticky wing-trap, and hung approximately six meters high in the outer walnut canopy. Trap liners and treatment HPV septa were replaced every 10–14 days and pheromone septa every month and tests were conducted throughout two summers.

A replicated series of different HPV treatment traps, control "blank" (unbaited) trap, and a commercial pheromone-baited trap (Trécé, Inc.) were distributed 5 trees apart throughout two distant Hartley walnut orchards and validated in 12 walnut orchards. The orchards were distinct, with one using three summer insecticide sprays and the other had no spraying. Thus, these test orchards had low vs. moderate relative populations of codling moths. Significant effects on the gender of codling moths captured were judged by paired tests, either T-test or a nonparametric test.

A second series of inherent attractancy tests were conducted on the most-active HPV blend (ester blend #10) using a novel, funnel-liquid (50:50 water and antifreeze) jar-trap adapted from a prototype of Trece, Inc., to rapidly kill (drown) attracted moths ("rapid-kill liquid traps"). This study comprised of a pheromone standard trap, a control blank trap and seven replicated HPV ester blend #10-baited traps. The rapid-kill traps were hung six meters high on trees distributed five rows apart in a Hartley walnut orchard with a moderate codling moth population. HPV ester blend #10 was loaded on a rubber septa at approximate doses of 10 mg/septum and were replaced every 10 days, while the commercial pheromone septum was replaced monthly.

Pheromone Preference Test

Pheromone traps (sticky wing traps, Trécé, Inc.,) were hung as pairs: a pheromone only baited-trap vs. a pheromone+HPV blend-baited trap. The two traps of a test pair were attached in close competitive proximity (120 cm apart) on a common hanger bar (PVC pipe). The paired-trap bars were hung 5–6 meters high on the outer canopies of trees. A single pair-trap was hung per tree and different replicate test trees were separated by five rows in a matrix through the orchard. Each pheromone trap was baited with ½ of a commercial pheromone-impregnated rubber septum (Trécé, Inc.). Septa were sectioned by a razor blade. The HPV blends evaporated from their own separate impregnated rubber septa containing 10 mg diluted in hexane/septum).

Tests were conducted in a Harley English walnut orchard. Tests spanned the entire two year seasons April–October with traps checked, males sexed, counted and removed every 2–7 days. Significant effect on pheromone trap capture were judged by paired tests either T-test or a nonparametric test.

EXAMPLE 3

Purification of Bisexual Attractants

This example illustrates purification procedure suitable for purification of host plant volatiles of the invention.

1. Purification of (2E,4Z)-2,4-decadienoate Acid

A. Hydrolysis of Ethyl (2E,4Z)-2,4-decadienoate

An aqueous solution of sodium hydroxide (10%, 22 ml) was added to a solution of technical grade ethyl (2E,4Z)-2,4-decadienoate (10 g) in tetrahydrofuran (100 ml). The mixture was heated under reflux for 5 hours with rapid stirring in a nitrogen atmosphere. After allowing to cool to room temperature, tetrahydrofuran was removed on a rotary evaporator, the residue was diluted with water (100 ml), and acidified to pH 2 with 6N HCl. The acid was extracted with ether (3×100 ml) and the combined extracts were washed with water (2×50 ml) and brine (50 ml) and dried using anhydrous magnesium sulfate. Removal of ether under reduced pressure gave (2E,4Z)-2,4-decadienoic acid. This product was used in the next step without further purification.

B. Preparation of the Cyclohexylamine Salt of (2E,4Z)-2,4-decadienoic Acid

Cyclohexylamine (5 g) was added dropwise at 0° C. with stirring to a solution of the crude acid above in hexane (100 ml). Stirring was continued for two hours at room temperature until the cyclohexylamine salt precipitated. The cyclohexylamine salt was isolated by filtration and washed with hexane (50 ml). This salt was crystallized three times from acetone.

C. Regeneration of the Pure (2E,4Z)-2,4-decadienoic Acid

The purified cyclohexylamine salt of (2E,4Z)-2,4-decadienoic acid was suspended in water (100 ml) and acidified pH 2 with 6N HCl. The acid was extracted with ether (3×100 ml) and the combined extracts were washed with water (2×50 ml) and brine (50 ml) and dried (anhydrous magnesium sulfate). Removal of ether under reduced pressure gave pure (2E,4Z)-2,4-decadienoic acid. Purity of the acid, determined by gas chromatography (GC) was >99%. The weight of the pure acid was 2.5 g.

2. Conversion of the Acid (2E,4Z)-2,4-decadienoic acid to Ethyl (2E,4Z)-2,4-decadienoate Oxalyl chloride (3.8 g, 2 eq.) was added dropwise at room temperature to a solution of pure (2E,4Z)-2,4-decadienoic acid (2.5 g) in anhydrous hexane (25 ml) in a nitrogen atmosphere. The solution was stirred at room temperature for three hours. The solvent and excess of oxalyl chloride were then removed in vacuo first on a rotary evaporator, and then at 0.1 mm Hg, keeping the temperature of the reaction mixture below room temperature. The acid chloride obtained was dissolved in hexane (25 ml) cooled in an ice bath, and then ethanol (absolute, 10 ml) was added with stirring in a nitrogen atmosphere. After stirring for an additional half hour at 0° C., the reaction mixture was quenched with a saturated aqueous solution of sodium bicarbonate (10 ml). The ethyl (2E,4Z)-2,4-decadienoate was extracted with ether (3×100 ml) and the combined extracts were washed with water (2×50 ml), brine (50 ml) and dried with anhydrous magnesium sulfate. Removal of ether and excess of ethanol under reduced pressure gave the pure ethyl (2E,4Z)-2,4-decadienoate (purity by GC was 96.7%).

Purification of ethyl (2E,4Z)-2,4-decadienoate by column chromatography on silica gel (70–230 mesh) and elution with 2% ethyl acetate in hexane gave material of 98.8% purity.

Methyl (2E,4Z)-2,4-decadienoate (purity 98.3%), n-propyl (2E,4Z)-2,4-decadienoate (purity 96.5%), and n-hexyl (2E,4Z)-2,4-decadienoate (purity 91.6%) were prepared by the same procedure using the appropriate alcohol in place of ethanol.

3. Preparation of (2E,4E)-2,4-decadienoate Acid and its Esters

Technical grade ethyl (2E,4Z)-2,4-decadienoate (50 g) was heated with thiophenol (0.5 g), under nitrogen, with stirring, for three hours at 100° C. to yield an equilibrium mixture of geometrical isomers.

The reaction mixture was hydrolyzed, and the major acid (2E,4E)-2,4-decadienoate acid was isolated via its cyclohexylamine salt following the procedure given above for the (2E,4Z)-isomer.

Methyl (2E,4E)-2,4-decadienoate (purity 100% by GC), ethyl (2E,4E)-2,4-decadienoate (purity 99.5%), n-propyl (2E,4E)-2,4-decadienoate (purity 98.5%), iso-propyl (2E,4E)-2,4-decadienoate (purity 99.2%), n-butyl (2E,4E)-2,4-decadienoate (purity 99.2%), n-hexyl (2E,4E)-2,4-decadienoate (purity >99.0%) were prepared following the same procedure used for the preparation of analogous esters in the (2E,4Z)-2,4 series.

What is claimed is:

1. A purified volatile bisexual attractant for adult insect and larvae of lepidopterous species consisting of ethyl (2E,4Z)-2,4-decadienoate in admixture with at least one compound selected from the group consisting of ethyl (2Z,4E)-2,4-decadienoate;
ethyl (2E,4E)-2,4-decadienoate;
ethyl (2Z,4Z)-2,4-decadienoate;
methyl (2E,4Z)-2,4-decadienoate;
methyl (2E,4E)-2,4-decadienoate;
propyl (2E,4Z)-2,4-decadienoate;
propyl (2E,4E)-2,4-decadienoate;
pentyl (2E,4Z)-2,4-decadienoate;
pentyl (2E,4E)-2,4-decadienoate;
butyl (2E,4Z)-2,4-decadienoate;
butyl (2E,4E)-2,4-decadienoate;
hexyl (2E,4Z)-2,4-decadienoate;
hexyl (2E,4E)-2,4-decadienoate;
isopropyl (2E,4Z)-2,4-decadienoate; and
isopropyl (2E,4E)-2,4-decadienoate;

wherein said attractant is purified to at least to 98.5% purity.

2. A purified volatile bisexual attractant for adult insect and larvae of lepidopterous species consisting of ethyl (2E,4Z)-2,4-decadienoate, methyl (2E,4Z)-2,4-decadienoate, methyl decanoate and ethyl decanoate, wherein said attractant is purified to at least 98.5% purity.

3. A formulation suitable for controlling and monitoring fruit and nut tree infestation or for disrupting the mating and host-finding of the adult insect or larvae of lepidopterous species, said formulation consisting essentially of ethyl (2E,4Z)-2,4-decadienoate in combination with
ethyl (2E,4E)-2,4-decadienoate;
ethyl (2Z,4E)-2,4-decadienoate;
ethyl (2Z,4Z)-2,4-decadienoate;
methyl (2E,4Z)-2,4-clecadienoate;
methyl (2E,4E)-2,4-decadienoate;
propyl (2E,4Z)-2,4-decadienoate;
propyl (2E,4E)-2,4-decadienoate;
butyl (2E,4Z)-2,4-decadienoate;
butyl (2E,4E)-2,4-decadienoate;
pentyl (2E,4Z)-2,4-decadienoate;
pentyl (2E,4E)-2,4-decadienoate;
hexyl (2E,4Z)-2,4-decadienoate;
hexyl (2E,4E)-2,4-decadienoate;
isopropyl (2E,4Z)-2,4-decadienoate or
isopropyl (2E,4E)-2,4-decadienoate, further in combination with an insecticide, pheromone or a mixture thereof and with an additive selected from the group consisting of an emulsifier, antioxidant, thickener, antifreeze agent, filler, solvent, ultraviolet absorber, UV blocking agent, dyestuff and a mixture thereof.

4. The formulation of claim 3 in a sprayable, solid or liquid form.

5. The formulation of claim 4 in the liquid or solid form for placement on the surface of or in a trap, a trap-like station, a trap-like enclosure or a trap-like platform.

6. A sprayable, solid or liquid formulation suitable for controlling and monitoring fruit and nut tree infestation or for disrupting the mating and host-finding of the adult insect or larvae of lepidopterous species, said formulation consisting essentially of ethyl(2E,4Z)-2,4-decadienoate in combination with an insecticide, pheromone or a mixture thereof and with an additive selected from the group consisting of an emulsifier, antioxidant, thickener, antifreeze agent, filler, solvent, ultraviolet absorber, UV blocking agent, dyestuff and a mixture thereof;

wherein the insecticide is selected from the group consisting of abamectin, acephate, acrinathrin, alanycarb, aldicarb, alphamethrin, amitraz, avermectin, azadirachtin, azinphos A, azinphos M, azocyclotin, Bacillus thuringiensis, bendiocarb, benfuracarb, bensultap, betacyfluthrin, bifenthrin, bioresmethrin, BPMC, brofenprox, bromophos A, bufencarb, buprofezin, butocarboxin, butylpyridaben, cadusafos, carbaryl, carbofuran, carbophenothion, carbosul fan, cartap, chlorethocarb, chlorethoxyfos, chlorfenvinphos, chlorfluazuron, chlormephos, chlorpyrifos, chlorpyrifos M, cis-resmethrin, clocythrin, clofentezine, cyanophos, cyclothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate,fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, nitenpyramomethoat, oxamyl, oxydemethon M, oxydeprofos, parathion A, parathion M, permethrin, phenothrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachiophos, pyridaphenthion, 11 pyresmethrin, pyrethrum, pyridaben, pyrimidifen, pyriproxifen, quinaiphos, resmethrin, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralocytrin, tralomethrin, triarathen, triazophos, triazuron, trichiorfon, triflumuron, trimethacarb, transfluthrin vamidothion, XMC, xylylcarb and zetamethrin.

7. The formulation of claim 6 wherein the pheromone is selected from the group consisting of (Z)-5-decenyl acetate, dodecenyl acetate, (Z)-7-dodecenyl acetate, (E)-7-dodecenyl acetate, (Z)-8-dodecenyl acetate, (E)-8-dodecenyl acetate, (Z)-9-dodecenyl acetate, (E)-9-dodecenyl acetate, (E)-10-dodecenyl acetate, 11-dodecenyl acetate, (Z)-9,11-dodecadienyl acetate, (E)-9,11-dodecadienyl acetate, (Z)-11-tridecenyl acetate, (E)-11-tridecenyl acetate, tetradecenyl acetate, (E)-7-tetradecenyl acetate, (Z)-8-tetradecenyl acetate, (E)-8-tetradecenyl acetate, (Z)-9-tetradecenyl acetate, (E)-9-tetradecenyl acetate, (Z)-10-tetradecenyl acetate, (E)-10-tetradecenyl acetate, (Z)-11-tetradecenyl acetate, (E)-11-tetradecenyl acetate, (Z)-12-pentadecenyl acetate, (E)-12-pentadecenyl acetate, hexadecenyl acetate, (Z)-7-hexadecenyl acetate, (Z)-11-hexadecenyl acetate, (E)-11-hexadecenyl acetate, octadecenyl acetate, (E,Z)-7,9-dodecadienyl acetate, (Z,E)-7,9-dodecadienyl acetate, (E,E)-7,9-dodecadienyl acetate, (Z,Z)-7,9-dodecadienyl acetate, (E,E)-8, 10-dodecadienyl acetate, (E,Z)-9,12-dodecadienyl acetate, (E,Z)-4,7-tridecadienyl acetate, (E,E)-9,11-tetradecadienyl acetate, (Z,Z)-9,12-tetradecadienyl acetate, (Z,Z)-7,11-hexadecadienyl acetate, (E,Z)-7,11-hexadecadienyl acetate, (Z,E)-7,11-hexadecadienyl acetate, (E,E)-7,11-hexadecadienyl acetate, (Z,E)-3,13-octadecadienyl acetate, (E,Z)-3,13-octadecadienyl acetate, (E,E)-3,13-octadecadienyl acetate, decanol, (Z)-6-nonenol, (E)-6-nonenol, dodecanol, (Z)-5-decenol, 11-dodecenol, (Z)-7-dedocenol, (E)-7-dodecenol, (Z)-8-dodecenol, (E)-8-dodecenol, (E)-9-dodecenol, (Z)-9-dodecenol, (E)-9,11-dodecadienol, (Z)-9,11-dodecadienol, (Z,E)-5,7-dodecadienol, (E,E)-5,7-dodecadienol, (E,E)-8,10-dodecadienol, (E,Z)-8,10-dodecadienol, (Z,Z)-8,10-dodecadienol, (Z,E)-8,10-dodecadienol, (E,Z)-7,9-dodecadienol, (Z,Z)-7,9-dodecadienol, (E)-5-tetradecenol, (Z)-8-tetradecenol, (Z)-9-tetradecenol, (E)-9-tetradecenol, (Z)-10-tetradecenol, (Z)-11-tetradecenol, (E)-11-tetradecenol, (Z)-11-hexadecenol, (Z,E)-9,11-tetradecadienol, (Z,E)-9,12-tetradecadienol, (Z,Z)-9,12-tetradecadienol, (Z,Z)-10,12-tetradecadienol, (Z,Z)-7,11-hexadecadienol, (Z,E)-7,11-hexadecadienol, (E)-14-methyl-B-hexadecen-1-ol, (Z)-14-methyl-8-hexadecen-1-ol, (E,E)-10,12-hexadecadienol, (E,Z)-10,12-hexadecadienol, dodecanal, (Z)-9-dodecanal, tetradecanal, (Z)-7-tetradecenal, (Z)-9-tetradecenal, (Z)-11-tetradecenal, (E)-11-tetradecenal, (E)-11,13-tetradecadienal, (E,E)-8,10-tetradecadienal, (Z,E)-9,11-tetradecadienal, (Z,E)-9,12-tetradecadienal, hexadecanal, (Z)-8-hexadecenal, (Z)-9-hexadecenal, (Z)-10-hexadecenal, (E)-10-hexadecenal, (Z)-11-hexadecenal, (E) hexadecenal, (Z)-12-hexadecenal, (Z)-13-hexadecenal, (Z)-14-methyl-8-hexadecenal, (E)-14-methyl-8-hexadecenal, (Z,Z)-7,11-hexadecadienal, (Z,E)-7,11-hexadecadienal,(Z,E)-9,11-hexadecadienal, (E,E)-10,12-hexadecadienal,(E,Z)-10,12-hexadecadienal, (Z,E)-10,12-hexadecadienal, (Z,Z)-10,12-hexadecadienal, (Z,Z)-11,13-hexadecadienal, octadecenal, (Z)-11-octadecenal, (E)-13-octadecenal, (Z)-13-octadecenal, (Z)-5-decenyl 3-methylbutanoate and (+) cis-7,8-epoxy-2-methyloctadecane.

8. The formulation of claim 7 wherein the pheromone is (E,E)-8,10-dodecadienol.

9. The formulation of claim 8 in sprayable form for spray coating of a surface of a trap, a trap-like station, a trap-like enclosure or a trap-like platform.

10. The formulation of claim 8 for a dispersion as droplets, microcapsules, a slow-release film, drops, puffers, blocks or monoliths.

11. A lure and kill insect formulation for attracting, capturing and killing insect pests of lepidopterous species comprising at least one attractant in combination with an insecticide, wherein said attractant is selected from the group consisting of
  methyl decanoate;
  ethyl (2E,4Z)-2,4-decadienoate;
  ethyl (2E,4E)-2,4-decadienoate;
  ethyl (2Z,4E)-2,4-decadienoate;
  ethyl (2Z,4Z)-2,4-decadienoate;
  methyl (2E,4Z)-2,4-decadienoate;
  methyl (2E,4E)-2,4-decadienoate;
  propyl (2E,4Z)-2,4-decadienoate;
  propyl (2E,4E)-2,4-decadienoate;
  butyl (2E,4Z)-2,4-decadienoate;
  butyl (2E,4E)-2,4-decadienoate;
  pentyl (2E,4Z)-2,4-decadienoate;
  pentyl (2E,4E)-2,4-decadienoate;
  hexyl (2E,4Z)-2,4-decadienoate;
  hexyl (2E,4E)-2,4-decadienoate;
  isopropyl (2E,4Z)-2,4-decadienoate; and
  isopropyl (2E,4E)-2,4-decadienoate; and
  wherein said insecticide is selected from the group consisting of abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, bioresmethrin, BFMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-Resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichiorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflu.muron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos,moxidectin, naled, NC 184, NI 25, nitenpyram omethoat, oxamyl, oxydemethon N, oxydeprofos, parathion A, parathion M,permethrin, phenothrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachiophos, pyridaphenthion, 11 pyresmethrin, pyrethrum, pyridaben, pyrimidifen, pyriproxifen, quinalphos, resmethrin, RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralocytrin, tralomethrin, triarathen, triazophos, triazuron, trichlorfon, triflumuron, trimethacarb, transfluthrin vamidothion, XMC, xylylcarb and zetamethrin.

12. The formulation of claim 11 wherein the attractant is ethyl (2E,4Z)-2,4-decadienoate.

13. The formulation of claim 12 wherein the insecticide is a pyrethroid selected from permethrin, cypermethrin, fenvalerate, fluvalinate, deltamethrin, cyfluthrin, transfluthrin or cyhalothrin.

14. The formulation of claim 13 wherein the insect pest is a codling moth.

* * * * *